(12) United States Patent
Schmid

(10) Patent No.: US 11,596,740 B2
(45) Date of Patent: *Mar. 7, 2023

(54) FLUID DELIVERY AND INFUSION DEVICES, AND METHODS OF USE THEREOF

(71) Applicant: Insulet Corporation, Acton, MA (US)

(72) Inventor: Kevin G. Schmid, Boxford, MA (US)

(73) Assignee: INSULET CORPORATION, Acton, MA (US)

( * ) Notice: Subject to any disclaimer, the term of this patent is extended or adjusted under 35 U.S.C. 154(b) by 325 days.

This patent is subject to a terminal disclaimer.

(21) Appl. No.: 16/902,511

(22) Filed: Jun. 16, 2020

(65) Prior Publication Data

US 2020/0306448 A1 Oct. 1, 2020

Related U.S. Application Data

(63) Continuation of application No. 15/047,028, filed on Feb. 18, 2016, now Pat. No. 10,737,024.
(Continued)

(51) Int. Cl.
*A61M 5/14* (2006.01)
*A61M 5/172* (2006.01)
(Continued)

(52) U.S. Cl.
CPC ...... *A61M 5/1723* (2013.01); *A61M 5/14248* (2013.01); *A61M 2005/1402* (2013.01);
(Continued)

(58) Field of Classification Search
CPC .......... A61M 5/14244; A61M 5/14248; A61M 2005/14208; G16H 20/17
See application file for complete search history.

(56) References Cited

U.S. PATENT DOCUMENTS

| 2,797,149 A | 6/1957 | Skeggs |
| 3,631,847 A | 1/1972 | Hobbs |

(Continued)

FOREIGN PATENT DOCUMENTS

| AU | 2015200834 A1 | 3/2015 |
| AU | 2015301146 A1 | 3/2017 |

(Continued)

OTHER PUBLICATIONS

US 5,954,699 A, 09/1999, Jost et al. (withdrawn)
(Continued)

*Primary Examiner* — Laura A Bouchelle
(74) *Attorney, Agent, or Firm* — Goodwin Procter LLP

(57) ABSTRACT

A medical device comprising an infusion device comprising a fluid reservoir to contain a therapeutic fluid and a transcutaneous access tool fluidly coupled to the fluid reservoir, the transcutaneous access tool configured to deliver the therapeutic fluid subcutaneously to a patient; wherein the infusion device operates in a stand-by mode prior to the therapeutic fluid being introduced into the fluid reservoir; wherein the infusion device operates to deploy the transcutaneous access tool within a predetermined deployment time period upon filling the fluid reservoir to a predetermined fill level with the therapeutic fluid.

20 Claims, 20 Drawing Sheets

Related U.S. Application Data

(60) Provisional application No. 62/117,937, filed on Feb. 18, 2015.

(51) Int. Cl.
   *A61M 5/142* (2006.01)
   *A61M 5/158* (2006.01)

(52) U.S. Cl.
   CPC ............ *A61M 2005/14208* (2013.01); *A61M 2005/14252* (2013.01); *A61M 2005/1585* (2013.01); *A61M 2005/1726* (2013.01)

(56) References Cited

U.S. PATENT DOCUMENTS

| | | |
|---|---|---|
| 3,634,039 A | 1/1972 | Brandy |
| 3,812,843 A | 5/1974 | Wootten et al. |
| 3,841,328 A | 10/1974 | Jensen |
| 4,055,175 A | 10/1977 | Clemens et al. |
| 4,146,029 A | 3/1979 | Ellinwood, Jr. |
| 4,151,845 A | 5/1979 | Clemens |
| 4,245,634 A | 1/1981 | Albisser et al. |
| 4,368,980 A | 1/1983 | Aldred et al. |
| 4,373,527 A | 2/1983 | Fischell |
| 4,403,984 A | 9/1983 | Ash et al. |
| 4,464,170 A | 8/1984 | Clemens et al. |
| 4,469,481 A | 9/1984 | Kobayashi |
| 4,475,901 A | 10/1984 | Kraegen et al. |
| 4,526,568 A | 7/1985 | Clemens et al. |
| 4,526,569 A | 7/1985 | Bernardi |
| 4,529,401 A | 7/1985 | Leslie et al. |
| 4,559,033 A | 12/1985 | Stephen et al. |
| 4,559,037 A | 12/1985 | Franetzki et al. |
| 4,573,968 A | 3/1986 | Parker |
| 4,624,661 A | 11/1986 | Arimond |
| 4,633,878 A | 1/1987 | Bombardieri |
| 4,657,529 A | 4/1987 | Prince et al. |
| 4,685,903 A | 8/1987 | Cable et al. |
| 4,731,726 A | 3/1988 | Mien, III |
| 4,743,243 A | 5/1988 | Vaillancourt |
| 4,755,173 A | 7/1988 | Konopka et al. |
| 4,781,688 A | 11/1988 | Thoma et al. |
| 4,781,693 A | 11/1988 | Martinez et al. |
| 4,808,161 A | 2/1989 | Kamen |
| 4,854,170 A | 8/1989 | Brimhall et al. |
| 4,886,499 A | 12/1989 | Cirelli et al. |
| 4,900,292 A | 2/1990 | Berry et al. |
| 4,919,596 A | 4/1990 | Slate et al. |
| 4,925,444 A | 5/1990 | Orkin et al. |
| 4,940,527 A | 7/1990 | Kazlauskas et al. |
| 4,975,581 A | 12/1990 | Robinson et al. |
| 4,976,720 A | 12/1990 | Machold et al. |
| 4,981,140 A | 1/1991 | Wyatt |
| 4,994,047 A | 2/1991 | Walker et al. |
| 5,007,286 A | 4/1991 | Malcolm et al. |
| 5,097,834 A | 3/1992 | Skrabal |
| 5,102,406 A | 4/1992 | Arnold |
| 5,109,850 A | 5/1992 | Blanco et al. |
| 5,125,415 A | 6/1992 | Bell |
| 5,134,079 A | 7/1992 | Cusack et al. |
| 5,165,406 A | 11/1992 | Wong |
| 5,176,662 A | 1/1993 | Bartholomew et al. |
| 5,178,609 A | 1/1993 | Ishikawa |
| 5,207,642 A | 5/1993 | Orkin et al. |
| 5,232,439 A | 8/1993 | Campbell et al. |
| 5,237,993 A | 8/1993 | Skrabal |
| 5,244,463 A | 9/1993 | Cordner, Jr. et al. |
| 5,257,980 A | 11/1993 | Van Antwerp et al. |
| 5,273,517 A | 12/1993 | Barone et al. |
| 5,281,808 A | 1/1994 | Kunkel |
| 5,299,571 A | 4/1994 | Mastrototaro |
| 5,308,982 A | 5/1994 | Ivaldi et al. |
| 5,342,298 A | 8/1994 | Michaels et al. |
| 5,377,674 A | 1/1995 | Kuestner |
| 5,380,665 A | 1/1995 | Cusack et al. |
| 5,385,539 A | 1/1995 | Maynard |
| 5,389,078 A | 2/1995 | Zalesky et al. |
| 5,411,889 A | 5/1995 | Hoots et al. |
| 5,468,727 A | 11/1995 | Phillips et al. |
| 5,505,709 A | 4/1996 | Funderburk et al. |
| 5,505,828 A | 4/1996 | Wong et al. |
| 5,507,288 A | 4/1996 | Bocker et al. |
| 5,533,389 A | 7/1996 | Kamen et al. |
| 5,558,640 A | 9/1996 | Pfeiler et al. |
| 5,569,186 A | 10/1996 | Lord et al. |
| 5,584,813 A | 12/1996 | Livingston et al. |
| 5,609,572 A | 3/1997 | Lang |
| 5,665,065 A | 9/1997 | Colman et al. |
| 5,678,539 A | 10/1997 | Schubert et al. |
| 5,685,844 A | 11/1997 | Marttila |
| 5,685,859 A | 11/1997 | Kornerup |
| 5,693,018 A | 12/1997 | Kriesel et al. |
| 5,697,899 A | 12/1997 | Hillman et al. |
| 5,700,695 A | 12/1997 | Yassinzadeh et al. |
| 5,703,364 A | 12/1997 | Rosenthal |
| 5,714,123 A | 2/1998 | Sohrab |
| 5,716,343 A | 2/1998 | Kriesel et al. |
| 5,722,397 A | 3/1998 | Eppstein |
| 5,741,228 A | 4/1998 | Lambrecht et al. |
| 5,746,217 A | 5/1998 | Erickson et al. |
| 5,755,682 A | 5/1998 | Knudson et al. |
| 5,758,643 A | 6/1998 | Wong et al. |
| 5,800,405 A | 9/1998 | McPhee |
| 5,800,420 A | 9/1998 | Gross et al. |
| 5,801,057 A | 9/1998 | Smart et al. |
| 5,804,048 A | 9/1998 | Wong et al. |
| 5,817,007 A | 10/1998 | Fodgaard et al. |
| 5,820,622 A | 10/1998 | Gross et al. |
| 5,823,951 A | 10/1998 | Messerschmidt |
| 5,840,020 A | 11/1998 | Heinonen et al. |
| 5,848,991 A | 12/1998 | Gross et al. |
| 5,851,197 A | 12/1998 | Marano et al. |
| 5,858,005 A | 1/1999 | Kriesel |
| 5,865,806 A | 2/1999 | Howell |
| 5,871,470 A | 2/1999 | McWha |
| 5,879,310 A | 3/1999 | Sopp et al. |
| 5,902,253 A | 5/1999 | Pfeiffer et al. |
| 5,931,814 A | 8/1999 | Alex et al. |
| 5,932,175 A | 8/1999 | Knute et al. |
| 5,935,099 A | 8/1999 | Peterson et al. |
| 5,947,911 A | 9/1999 | Wong et al. |
| 5,971,941 A | 10/1999 | Simons et al. |
| 5,993,423 A | 11/1999 | Choi |
| 5,997,501 A | 12/1999 | Gross et al. |
| 6,017,318 A | 1/2000 | Gauthier et al. |
| 6,024,539 A | 2/2000 | Blomquist |
| 6,032,059 A | 2/2000 | Henning et al. |
| 6,036,924 A | 3/2000 | Simons et al. |
| 6,040,578 A | 3/2000 | Malin et al. |
| 6,049,727 A | 4/2000 | Grothall |
| 6,050,978 A | 4/2000 | Orr et al. |
| 6,058,934 A | 5/2000 | Sullivan |
| 6,066,103 A | 5/2000 | Duchon et al. |
| 6,071,292 A | 6/2000 | Makower et al. |
| 6,072,180 A | 6/2000 | Kramer et al. |
| 6,077,055 A | 6/2000 | Vilks |
| 6,090,092 A | 7/2000 | Fowles et al. |
| 6,101,406 A | 8/2000 | Hacker et al. |
| 6,102,872 A | 8/2000 | Doneen et al. |
| 6,115,673 A | 9/2000 | Malin et al. |
| 6,123,827 A | 9/2000 | Wong et al. |
| 6,124,134 A | 9/2000 | Stark |
| 6,126,637 A | 10/2000 | Kriesel et al. |
| 6,128,519 A | 10/2000 | Say |
| 6,142,939 A | 11/2000 | Eppstein et al. |
| 6,143,164 A | 11/2000 | Heller et al. |
| 6,157,041 A | 12/2000 | Thomas et al. |
| 6,161,028 A | 12/2000 | Braig et al. |
| 6,162,639 A | 12/2000 | Douglas |
| 6,196,046 B1 | 3/2001 | Braig et al. |
| 6,200,287 B1 | 3/2001 | Keller et al. |
| 6,200,338 B1 | 3/2001 | Solomon et al. |
| 6,214,629 B1 | 4/2001 | Freitag et al. |
| 6,226,082 B1 | 5/2001 | Roe |

(56) References Cited

U.S. PATENT DOCUMENTS

| | | |
|---|---|---|
| 6,244,776 B1 | 6/2001 | Wiley |
| 6,261,065 B1 | 7/2001 | Nayak et al. |
| 6,262,798 B1 | 7/2001 | Shepherd et al. |
| 6,270,455 B1 | 8/2001 | Brown |
| 6,271,045 B1 | 8/2001 | Douglas et al. |
| 6,280,381 B1 | 8/2001 | Malin et al. |
| 6,285,448 B1 | 9/2001 | Kuenstner |
| 6,309,370 B1 | 10/2001 | Haim et al. |
| 6,312,888 B1 | 11/2001 | Wong et al. |
| 6,334,851 B1 | 1/2002 | Hayes et al. |
| 6,375,627 B1 | 4/2002 | Mauze et al. |
| 6,379,301 B1 | 4/2002 | Worthington et al. |
| 6,402,689 B1 | 6/2002 | Scarantino et al. |
| 6,470,279 B1 | 10/2002 | Samsoondar |
| 6,475,196 B1 | 11/2002 | Vachon |
| 6,477,901 B1 | 11/2002 | Tadigadapa et al. |
| 6,484,044 B1 | 11/2002 | Lilienfeld-Toal |
| 6,491,656 B1 | 12/2002 | Morris |
| 6,512,937 B2 | 1/2003 | Blank et al. |
| 6,525,509 B1 | 2/2003 | Petersson et al. |
| 6,528,809 B1 | 3/2003 | Thomas et al. |
| 6,540,672 B1 | 4/2003 | Simonsen et al. |
| 6,544,212 B2 | 4/2003 | Galley et al. |
| 6,546,268 B1 | 4/2003 | Ishikawa et al. |
| 6,546,269 B1 | 4/2003 | Kurnik |
| 6,553,841 B1 | 4/2003 | Blouch |
| 6,554,798 B1 | 4/2003 | Mann et al. |
| 6,556,850 B1 | 4/2003 | Braig et al. |
| 6,558,351 B1 | 5/2003 | Steil et al. |
| 6,560,471 B1 | 5/2003 | Heller et al. |
| 6,561,978 B1 | 5/2003 | Conn et al. |
| 6,562,001 B2 | 5/2003 | Lebel et al. |
| 6,562,014 B2 | 5/2003 | Lin et al. |
| 6,569,125 B2 | 5/2003 | Jepson et al. |
| 6,572,542 B1 | 6/2003 | Houben et al. |
| 6,572,545 B2 | 6/2003 | Knobbe et al. |
| 6,574,490 B2 | 6/2003 | Abbink et al. |
| 6,575,905 B2 | 6/2003 | Knobbe et al. |
| 6,580,934 B1 | 6/2003 | Braig et al. |
| 6,618,603 B2 | 9/2003 | Varalli et al. |
| 6,633,772 B2 | 10/2003 | Ford et al. |
| 6,645,142 B2 | 11/2003 | Braig et al. |
| 6,653,091 B1 | 11/2003 | Dunn et al. |
| 6,662,030 B2 | 12/2003 | Khalil et al. |
| 6,669,663 B1 | 12/2003 | Thompson |
| 6,678,542 B2 | 1/2004 | Braig et al. |
| 6,699,221 B2 | 3/2004 | Vaillancourt |
| 6,718,189 B2 | 4/2004 | Rohrscheib et al. |
| 6,721,582 B2 | 4/2004 | Trepagnier et al. |
| 6,728,560 B2 | 4/2004 | Kollias et al. |
| 6,740,059 B2 | 5/2004 | Flaherty |
| 6,740,072 B2 | 5/2004 | Starkweather et al. |
| 6,751,490 B2 | 6/2004 | Esenaliev et al. |
| 6,758,835 B2 | 7/2004 | Close et al. |
| 6,780,156 B2 | 8/2004 | Haueter et al. |
| 6,810,290 B2 | 10/2004 | Lebel et al. |
| 6,837,858 B2 | 1/2005 | Cunningham et al. |
| 6,837,988 B2 | 1/2005 | Leong et al. |
| 6,846,288 B2 | 1/2005 | Nagar et al. |
| 6,862,534 B2 | 3/2005 | Sterling et al. |
| 6,865,408 B1 | 3/2005 | Abbink et al. |
| 6,890,291 B2 | 5/2005 | Robinson et al. |
| 6,936,029 B2 | 8/2005 | Mann et al. |
| 6,949,081 B1 | 9/2005 | Chance |
| 6,958,809 B2 | 10/2005 | Sterling et al. |
| 6,989,891 B2 | 1/2006 | Braig et al. |
| 6,990,366 B2 | 1/2006 | Say et al. |
| 7,004,404 B2 | 3/2006 | Nakajima |
| 7,009,180 B2 | 3/2006 | Sterling et al. |
| 7,016,713 B2 | 3/2006 | Gardner et al. |
| 7,025,743 B2 | 4/2006 | Mann et al. |
| 7,025,744 B2 | 4/2006 | Utterberg et al. |
| 7,027,848 B2 | 4/2006 | Robinson et al. |
| 7,043,288 B2 | 5/2006 | Davis, III et al. |
| 7,060,059 B2 | 6/2006 | Keith et al. |
| 7,061,593 B2 | 6/2006 | Braig et al. |
| 7,096,124 B2 | 8/2006 | Sterling et al. |
| 7,115,205 B2 | 10/2006 | Robinson et al. |
| 7,128,727 B2 | 10/2006 | Flaherty et al. |
| 7,139,593 B2 | 11/2006 | Kavak et al. |
| 7,139,598 B2 | 11/2006 | Hull et al. |
| 7,171,252 B1 | 1/2007 | Scarantino et al. |
| 7,190,988 B2 | 3/2007 | Say et al. |
| 7,204,823 B2 | 4/2007 | Estes et al. |
| 7,248,912 B2 | 7/2007 | Gough et al. |
| 7,267,665 B2 | 9/2007 | Steil et al. |
| 7,271,912 B2 | 9/2007 | Sterling et al. |
| 7,278,983 B2 | 10/2007 | Ireland et al. |
| 7,291,107 B2 | 11/2007 | Hellwig et al. |
| 7,291,497 B2 | 11/2007 | Holmes et al. |
| 7,303,549 B2 | 12/2007 | Flaherty et al. |
| 7,303,622 B2 | 12/2007 | Loch et al. |
| 7,303,922 B2 | 12/2007 | Jeng et al. |
| 7,354,420 B2 | 4/2008 | Steil et al. |
| 7,388,202 B2 | 6/2008 | Sterling et al. |
| 7,402,153 B2 | 7/2008 | Steil et al. |
| 7,404,796 B2 | 7/2008 | Ginsberg |
| 7,429,255 B2 | 9/2008 | Thompson |
| 7,460,130 B2 | 12/2008 | Salganicoff |
| 7,481,787 B2 | 1/2009 | Gable et al. |
| 7,491,187 B2 | 2/2009 | Van Den Berghe et al. |
| 7,500,949 B2 | 3/2009 | Gottlieb et al. |
| 7,509,156 B2 | 3/2009 | Flanders |
| 7,547,281 B2 | 6/2009 | Hayes et al. |
| 7,569,030 B2 | 8/2009 | Lebel et al. |
| 7,608,042 B2 | 10/2009 | Goldberger et al. |
| 7,651,845 B2 | 1/2010 | Doyle, III et al. |
| 7,680,529 B2 | 3/2010 | Kroll |
| 7,734,323 B2 | 6/2010 | Blomquist et al. |
| 7,766,829 B2 | 8/2010 | Sloan et al. |
| 7,785,258 B2 | 8/2010 | Braig et al. |
| 7,806,854 B2 | 10/2010 | Damiano et al. |
| 7,806,886 B2 | 10/2010 | Kanderian, Jr. et al. |
| 7,918,825 B2 | 4/2011 | OConnor et al. |
| 7,946,985 B2 | 5/2011 | Mastrototaro et al. |
| 7,972,296 B2 | 7/2011 | Braig et al. |
| 8,221,345 B2 | 7/2012 | Blomquist |
| 8,251,907 B2 | 8/2012 | Sterling et al. |
| 8,449,524 B2 | 5/2013 | Braig et al. |
| 8,452,359 B2 | 5/2013 | Rebec et al. |
| 8,454,576 B2 | 6/2013 | Mastrototaro et al. |
| 8,467,980 B2 | 6/2013 | Campbell et al. |
| 8,478,557 B2 | 7/2013 | Hayter et al. |
| 8,597,274 B2 | 12/2013 | Sloan et al. |
| 8,622,988 B2 | 1/2014 | Hayter |
| 8,810,394 B2 | 8/2014 | Kalpin |
| 9,171,343 B1 | 10/2015 | Fischell et al. |
| 9,233,204 B2 | 1/2016 | Booth et al. |
| 9,486,571 B2 | 11/2016 | Rosinko et al. |
| 9,579,456 B2 | 2/2017 | Budiman et al. |
| 9,743,224 B2 | 8/2017 | San Vicente et al. |
| 9,907,515 B2 | 3/2018 | Doyle, III et al. |
| 9,980,140 B1 | 5/2018 | Spencer et al. |
| 9,984,773 B2 | 5/2018 | Gondhalekar et al. |
| 10,248,839 B2 | 4/2019 | Levy et al. |
| 10,335,464 B1 | 7/2019 | Michelich et al. |
| 10,583,250 B2 | 3/2020 | Mazlish et al. |
| 10,737,024 B2 * | 8/2020 | Schmid ............ A61M 5/14248 |
| 10,987,468 B2 | 4/2021 | Mazlish et al. |
| 11,197,964 B2 | 12/2021 | Sjolund et al. |
| 11,260,169 B2 | 3/2022 | Estes |
| 2001/0021803 A1 | 9/2001 | Blank et al. |
| 2001/0051377 A1 | 12/2001 | Hammer et al. |
| 2001/0053895 A1 | 12/2001 | Vaillancourt |
| 2002/0010401 A1 | 1/2002 | Bushmakin et al. |
| 2002/0010423 A1 | 1/2002 | Gross et al. |
| 2002/0040208 A1 | 4/2002 | Flaherty et al. |
| 2002/0123740 A1 | 9/2002 | Flaherty et al. |
| 2002/0128543 A1 | 9/2002 | Leonhardt |
| 2002/0147423 A1 | 10/2002 | Burbank et al. |
| 2002/0155425 A1 | 10/2002 | Han et al. |
| 2002/0161288 A1 | 10/2002 | Shin et al. |
| 2003/0023148 A1 | 1/2003 | Lorenz et al. |
| 2003/0050621 A1 | 3/2003 | Lebel et al. |

(56) References Cited

U.S. PATENT DOCUMENTS

| | | |
|---|---|---|
| 2003/0060692 A1 | 3/2003 | L. Ruchti et al. |
| 2003/0086074 A1 | 5/2003 | Braig et al. |
| 2003/0086075 A1 | 5/2003 | Braig et al. |
| 2003/0090649 A1 | 5/2003 | Sterling et al. |
| 2003/0100040 A1 | 5/2003 | Bonnecaze et al. |
| 2003/0130616 A1 | 7/2003 | Steil et al. |
| 2003/0135388 A1 | 7/2003 | Martucci et al. |
| 2003/0144582 A1 | 7/2003 | Cohen et al. |
| 2003/0163097 A1 | 8/2003 | Fleury et al. |
| 2003/0195404 A1 | 10/2003 | Knobbe et al. |
| 2003/0208113 A1 | 11/2003 | Mault et al. |
| 2003/0208154 A1 | 11/2003 | Close et al. |
| 2003/0212379 A1 | 11/2003 | Bylund et al. |
| 2003/0216627 A1 | 11/2003 | Lorenz et al. |
| 2004/0034295 A1 | 2/2004 | Salganicoff |
| 2004/0045879 A1 | 3/2004 | Shults et al. |
| 2004/0051368 A1 | 3/2004 | Caputo et al. |
| 2004/0064259 A1 | 4/2004 | Haaland et al. |
| 2004/0097796 A1 | 5/2004 | Berman et al. |
| 2004/0116847 A1 | 6/2004 | Wall |
| 2004/0122353 A1 | 6/2004 | Shahmirian et al. |
| 2004/0133166 A1 | 7/2004 | Moberg et al. |
| 2004/0147034 A1 | 7/2004 | Gore et al. |
| 2004/0171983 A1 | 9/2004 | Sparks et al. |
| 2004/0203357 A1 | 10/2004 | Nassimi |
| 2004/0204868 A1 | 10/2004 | Maynard et al. |
| 2004/0215492 A1 | 10/2004 | Choi |
| 2004/0220517 A1 | 11/2004 | Starkweather et al. |
| 2004/0241736 A1 | 12/2004 | Hendee et al. |
| 2004/0249308 A1 | 12/2004 | Forssell |
| 2005/0003470 A1 | 1/2005 | Nelson et al. |
| 2005/0020980 A1 | 1/2005 | Inoue et al. |
| 2005/0022274 A1 | 1/2005 | Campbell et al. |
| 2005/0033148 A1 | 2/2005 | Haueter et al. |
| 2005/0049179 A1 | 3/2005 | Davidson et al. |
| 2005/0065464 A1 | 3/2005 | Talbot et al. |
| 2005/0065465 A1 | 3/2005 | Lebel et al. |
| 2005/0105095 A1 | 5/2005 | Pesach et al. |
| 2005/0137573 A1 | 6/2005 | McLaughlin |
| 2005/0171503 A1 | 8/2005 | Van Den Berghe et al. |
| 2005/0182306 A1 | 8/2005 | Sloan |
| 2005/0192494 A1 | 9/2005 | Ginsberg |
| 2005/0192557 A1 | 9/2005 | Brauker et al. |
| 2005/0197621 A1 | 9/2005 | Poulsen et al. |
| 2005/0203360 A1 | 9/2005 | Brauker et al. |
| 2005/0203461 A1 | 9/2005 | Flaherty et al. |
| 2005/0261660 A1 | 11/2005 | Choi |
| 2005/0272640 A1 | 12/2005 | Doyle et al. |
| 2005/0277912 A1 | 12/2005 | John |
| 2006/0009727 A1 | 1/2006 | OMahony et al. |
| 2006/0079809 A1 | 4/2006 | Goldberger et al. |
| 2006/0100494 A1 | 5/2006 | Kroll |
| 2006/0134323 A1 | 6/2006 | OBrien |
| 2006/0167350 A1 | 7/2006 | Monfre et al. |
| 2006/0189925 A1 | 8/2006 | Gable et al. |
| 2006/0189926 A1 | 8/2006 | Hall et al. |
| 2006/0197015 A1 | 9/2006 | Sterling et al. |
| 2006/0200070 A1 | 9/2006 | Callicoat et al. |
| 2006/0204535 A1 | 9/2006 | Johnson |
| 2006/0229531 A1 | 10/2006 | Goldberger et al. |
| 2006/0253085 A1 | 11/2006 | Geismar et al. |
| 2006/0264895 A1 | 11/2006 | Flanders |
| 2006/0276771 A1 | 12/2006 | Galley et al. |
| 2007/0016127 A1 | 1/2007 | Staib et al. |
| 2007/0060796 A1 | 3/2007 | Kim |
| 2007/0060869 A1 | 3/2007 | Tolle et al. |
| 2007/0060872 A1 | 3/2007 | Hall et al. |
| 2007/0083160 A1 | 4/2007 | Hall et al. |
| 2007/0106135 A1 | 5/2007 | Sloan et al. |
| 2007/0116601 A1 | 5/2007 | Patton |
| 2007/0129690 A1 | 6/2007 | Rosenblatt et al. |
| 2007/0142720 A1 | 6/2007 | Ridder et al. |
| 2007/0173761 A1 | 7/2007 | Kanderian et al. |
| 2007/0173974 A1 | 7/2007 | Lin |
| 2007/0179352 A1 | 8/2007 | Randlov et al. |
| 2007/0191716 A1 | 8/2007 | Goldberger et al. |
| 2007/0197163 A1 | 8/2007 | Robertson |
| 2007/0225675 A1 | 9/2007 | Robinson et al. |
| 2007/0244381 A1 | 10/2007 | Robinson et al. |
| 2007/0249007 A1 | 10/2007 | Rosero |
| 2007/0264707 A1 | 11/2007 | Liederman et al. |
| 2007/0282269 A1 | 12/2007 | Carter et al. |
| 2007/0287985 A1 | 12/2007 | Estes et al. |
| 2007/0293843 A1 | 12/2007 | Ireland et al. |
| 2008/0033272 A1 | 2/2008 | Gough et al. |
| 2008/0051764 A1 | 2/2008 | Dent et al. |
| 2008/0058625 A1 | 3/2008 | McGarraugh et al. |
| 2008/0065050 A1 | 3/2008 | Sparks et al. |
| 2008/0071157 A1 | 3/2008 | McGarraugh et al. |
| 2008/0071158 A1 | 3/2008 | McGarraugh et al. |
| 2008/0078400 A1 | 4/2008 | Martens et al. |
| 2008/0097289 A1 | 4/2008 | Steil et al. |
| 2008/0132880 A1 | 6/2008 | Buchman |
| 2008/0161664 A1 | 7/2008 | Mastrototaro et al. |
| 2008/0172026 A1 | 7/2008 | Blomquist |
| 2008/0177165 A1 | 7/2008 | Blomquist et al. |
| 2008/0188796 A1 | 8/2008 | Steil et al. |
| 2008/0200838 A1 | 8/2008 | Goldberger et al. |
| 2008/0208113 A1 | 8/2008 | Damiano et al. |
| 2008/0214919 A1 | 9/2008 | Harmon et al. |
| 2008/0228056 A1 | 9/2008 | Blomquist et al. |
| 2008/0249386 A1 | 10/2008 | Besterman et al. |
| 2008/0269585 A1 | 10/2008 | Ginsberg |
| 2008/0269714 A1 | 10/2008 | Mastrototaro et al. |
| 2008/0269723 A1 | 10/2008 | Mastrototaro et al. |
| 2008/0287906 A1 | 11/2008 | Burkholz et al. |
| 2009/0006061 A1 | 1/2009 | Thukral et al. |
| 2009/0018406 A1 | 1/2009 | Yodfat et al. |
| 2009/0030398 A1 | 1/2009 | Yodfat et al. |
| 2009/0036753 A1 | 2/2009 | King |
| 2009/0043240 A1 | 2/2009 | Robinson et al. |
| 2009/0054753 A1 | 2/2009 | Robinson et al. |
| 2009/0069743 A1 | 3/2009 | Krishnamoorthy et al. |
| 2009/0069745 A1 | 3/2009 | Estes et al. |
| 2009/0069787 A1 | 3/2009 | Estes et al. |
| 2009/0099521 A1 | 4/2009 | Gravesen et al. |
| 2009/0105573 A1 | 4/2009 | Malecha |
| 2009/0131861 A1 | 5/2009 | Braig et al. |
| 2009/0156922 A1 | 6/2009 | Goldberger et al. |
| 2009/0156924 A1 | 6/2009 | Shariati et al. |
| 2009/0163781 A1 | 6/2009 | Say et al. |
| 2009/0198350 A1 | 8/2009 | Thiele |
| 2009/0221890 A1 | 9/2009 | Saffer et al. |
| 2009/0228214 A1 | 9/2009 | Say et al. |
| 2009/0326343 A1 | 12/2009 | Gable et al. |
| 2010/0114026 A1 | 5/2010 | Karratt et al. |
| 2010/0121170 A1 | 5/2010 | Rule |
| 2010/0137784 A1 | 6/2010 | Cefai et al. |
| 2010/0152658 A1 | 6/2010 | Hanson et al. |
| 2010/0174228 A1 | 7/2010 | Buckingham et al. |
| 2010/0228110 A1 | 9/2010 | Tsoukalis |
| 2010/0262117 A1 | 10/2010 | Magni et al. |
| 2010/0262434 A1 | 10/2010 | Shaya |
| 2010/0295686 A1 | 11/2010 | Sloan et al. |
| 2010/0298765 A1 | 11/2010 | Budiman et al. |
| 2011/0021584 A1 | 1/2011 | Berggren et al. |
| 2011/0028817 A1 | 2/2011 | Jin et al. |
| 2011/0054390 A1 | 3/2011 | Searle et al. |
| 2011/0054399 A1 | 3/2011 | Chong et al. |
| 2011/0124996 A1 | 5/2011 | Reinke et al. |
| 2011/0144586 A1 | 6/2011 | Michaud et al. |
| 2011/0218495 A1* | 9/2011 | Remde .................. G16H 20/17 604/151 |
| 2011/0230833 A1 | 9/2011 | Landman et al. |
| 2011/0251509 A1 | 10/2011 | Beyhan et al. |
| 2011/0313680 A1 | 12/2011 | Doyle et al. |
| 2011/0316562 A1 | 12/2011 | Cefai et al. |
| 2012/0003935 A1 | 1/2012 | Lydon et al. |
| 2012/0030393 A1 | 2/2012 | Ganesh et al. |
| 2012/0078067 A1 | 3/2012 | Kovatchev et al. |
| 2012/0078161 A1 | 3/2012 | Masterson et al. |
| 2012/0078181 A1 | 3/2012 | Smith et al. |
| 2012/0101451 A1 | 4/2012 | Boit et al. |
| 2012/0123234 A1 | 5/2012 | Atlas et al. |

(56) References Cited

U.S. PATENT DOCUMENTS

| | | |
|---|---|---|
| 2012/0136336 A1 | 5/2012 | Mastrototaro et al. |
| 2012/0190955 A1 | 7/2012 | Rao et al. |
| 2012/0203085 A1 | 8/2012 | Rebec |
| 2012/0215087 A1 | 8/2012 | Cobelli et al. |
| 2012/0225134 A1 | 9/2012 | Komorowski |
| 2012/0226259 A1 | 9/2012 | Yodfat et al. |
| 2012/0232520 A1 | 9/2012 | Sloan et al. |
| 2012/0238851 A1 | 9/2012 | Kamen et al. |
| 2012/0271655 A1 | 10/2012 | Knobel et al. |
| 2012/0277668 A1 | 11/2012 | Chawla et al. |
| 2013/0030358 A1 | 1/2013 | Yodfat et al. |
| 2013/0158503 A1 | 6/2013 | Kanderian, Jr. et al. |
| 2013/0178791 A1 | 7/2013 | Javitt |
| 2013/0231642 A1 | 9/2013 | Doyle et al. |
| 2013/0261406 A1 | 10/2013 | Rebec et al. |
| 2013/0296823 A1 | 11/2013 | Melker et al. |
| 2014/0005633 A1 | 1/2014 | Finan |
| 2014/0066886 A1 | 3/2014 | Roy et al. |
| 2014/0074033 A1 | 3/2014 | Sonderegger et al. |
| 2014/0121635 A1 | 5/2014 | Hayter |
| 2014/0128839 A1 | 5/2014 | Dilanni et al. |
| 2014/0135880 A1 | 5/2014 | Baumgartner et al. |
| 2014/0146202 A1 | 5/2014 | Boss et al. |
| 2014/0180203 A1 | 6/2014 | Budiman et al. |
| 2014/0180240 A1 | 6/2014 | Finan et al. |
| 2014/0200426 A1 | 7/2014 | Taub et al. |
| 2014/0200559 A1 | 7/2014 | Doyle et al. |
| 2014/0276554 A1 | 9/2014 | Finan et al. |
| 2014/0276556 A1 | 9/2014 | Saint et al. |
| 2014/0278123 A1 | 9/2014 | Prodhom et al. |
| 2014/0309615 A1 | 10/2014 | Mazlish |
| 2014/0316379 A1 | 10/2014 | Sonderegger et al. |
| 2014/0325065 A1 | 10/2014 | Birtwhistle et al. |
| 2015/0018633 A1 | 1/2015 | Kovachev et al. |
| 2015/0025329 A1 | 1/2015 | Amarasingham et al. |
| 2015/0025495 A1 | 1/2015 | Peyser |
| 2015/0120317 A1 | 4/2015 | Mayou et al. |
| 2015/0134265 A1 | 5/2015 | Kohlbrecher et al. |
| 2015/0165119 A1 | 6/2015 | Palerm et al. |
| 2015/0173674 A1 | 6/2015 | Hayes et al. |
| 2015/0213217 A1 | 7/2015 | Amarasingham et al. |
| 2015/0217052 A1 | 8/2015 | Keenan et al. |
| 2015/0217053 A1 | 8/2015 | Booth et al. |
| 2015/0306314 A1 | 10/2015 | Doyle et al. |
| 2015/0351671 A1 | 12/2015 | Vanslyke et al. |
| 2015/0366945 A1 | 12/2015 | Greene |
| 2016/0015891 A1 | 1/2016 | Papiorek |
| 2016/0038673 A1 | 2/2016 | Morales |
| 2016/0038689 A1 | 2/2016 | Lee et al. |
| 2016/0051749 A1 | 2/2016 | Istoc |
| 2016/0082187 A1 | 3/2016 | Schaible et al. |
| 2016/0089494 A1 | 3/2016 | Guerrini |
| 2016/0175520 A1 | 6/2016 | Palerm et al. |
| 2016/0228641 A1 | 8/2016 | Gescheit et al. |
| 2016/0243318 A1 | 8/2016 | Despa et al. |
| 2016/0256087 A1 | 9/2016 | Doyle et al. |
| 2016/0287512 A1 | 10/2016 | Cooper et al. |
| 2016/0302054 A1 | 10/2016 | Kimura et al. |
| 2016/0354543 A1 | 12/2016 | Cinar et al. |
| 2017/0049386 A1 | 2/2017 | Abraham et al. |
| 2017/0143899 A1 | 5/2017 | Gondhalekar et al. |
| 2017/0143900 A1 | 5/2017 | Rioux et al. |
| 2017/0156682 A1 | 6/2017 | Doyle et al. |
| 2017/0173261 A1 | 6/2017 | O'Connor et al. |
| 2017/0281877 A1 | 10/2017 | Marlin et al. |
| 2017/0296746 A1 | 10/2017 | Chen et al. |
| 2017/0311903 A1 | 11/2017 | Davis et al. |
| 2017/0348482 A1 | 12/2017 | Duke et al. |
| 2018/0040255 A1 | 2/2018 | Freeman et al. |
| 2018/0075200 A1 | 3/2018 | Davis et al. |
| 2018/0075201 A1 | 3/2018 | Davis et al. |
| 2018/0075202 A1 | 3/2018 | Davis et al. |
| 2018/0092576 A1 | 4/2018 | Ambrosio et al. |
| 2018/0126073 A1 | 5/2018 | Wu et al. |
| 2018/0169334 A1 | 6/2018 | Grosman et al. |
| 2018/0200434 A1 | 7/2018 | Mazlish et al. |
| 2018/0200438 A1 | 7/2018 | Mazlish et al. |
| 2018/0200441 A1 | 7/2018 | Desborough et al. |
| 2018/0277253 A1 | 9/2018 | Gondhalekar et al. |
| 2018/0289891 A1 | 10/2018 | Finan et al. |
| 2018/0296757 A1 | 10/2018 | Finan et al. |
| 2018/0342317 A1 | 11/2018 | Skirble et al. |
| 2018/0369479 A1 | 12/2018 | Hayter et al. |
| 2019/0076600 A1 | 3/2019 | Grosman et al. |
| 2019/0240403 A1 | 8/2019 | Palerm et al. |
| 2019/0290844 A1 | 9/2019 | Monirabbasi et al. |
| 2019/0336683 A1 | 11/2019 | O'Connor et al. |
| 2019/0336684 A1 | 11/2019 | O'Connor et al. |
| 2019/0348157 A1 | 11/2019 | Booth et al. |
| 2020/0046268 A1 | 2/2020 | Patek et al. |
| 2020/0101222 A1 | 4/2020 | Lintereur et al. |
| 2020/0101223 A1 | 4/2020 | Lintereur et al. |
| 2020/0101225 A1 | 4/2020 | O'Connor et al. |
| 2020/0219625 A1 | 7/2020 | Kahlbaugh |
| 2020/0342974 A1 | 10/2020 | Chen et al. |
| 2021/0050085 A1 | 2/2021 | Hayter et al. |
| 2021/0098105 A1 | 4/2021 | Lee et al. |
| 2022/0023536 A1 | 1/2022 | Graham et al. |

FOREIGN PATENT DOCUMENTS

| | | |
|---|---|---|
| CN | 1297140 A | 5/2001 |
| DE | 19756872 A1 | 7/1999 |
| EP | 0341049 A2 | 11/1989 |
| EP | 0496305 A2 | 7/1992 |
| EP | 0549341 A1 | 6/1993 |
| EP | 1491144 A1 | 12/2004 |
| EP | 1571582 A2 | 9/2005 |
| EP | 0801578 B1 | 7/2006 |
| EP | 2666520 A1 | 10/2009 |
| EP | 2139382 A1 | 1/2010 |
| EP | 2397181 A1 | 12/2011 |
| EP | 2695573 A2 | 2/2014 |
| EP | 2830499 A1 | 2/2015 |
| EP | 2943149 A1 | 11/2015 |
| EP | 3177344 A1 | 6/2017 |
| EP | 3314548 A1 | 5/2018 |
| EP | 2897071 B1 | 5/2019 |
| EP | 3607985 A1 | 2/2020 |
| GB | 2443261 A | 4/2008 |
| JP | 51125993 A | 11/1976 |
| JP | 02131777 A | 5/1990 |
| JP | 2004283378 A | 10/2004 |
| JP | 2017525451 A | 9/2017 |
| JP | 2018153569 A | 10/2018 |
| JP | 2019525276 A | 9/2019 |
| TW | 200740148 A | 10/2007 |
| TW | M452390 U | 5/2013 |
| WO | 9800193 A1 | 1/1998 |
| WO | 9956803 A1 | 11/1999 |
| WO | 0030705 A1 | 6/2000 |
| WO | 0032258 A1 | 6/2000 |
| WO | 0172354 A2 | 10/2001 |
| WO | 2002015954 A1 | 2/2002 |
| WO | 0243866 A2 | 6/2002 |
| WO | 02082990 A1 | 10/2002 |
| WO | 03016882 A1 | 2/2003 |
| WO | 03039362 A1 | 5/2003 |
| WO | 03045233 A1 | 6/2003 |
| WO | 2004043250 A1 | 5/2004 |
| WO | 04092715 A1 | 10/2004 |
| WO | 2005051170 A2 | 6/2005 |
| WO | 2005082436 A1 | 9/2005 |
| WO | 05110601 A1 | 11/2005 |
| WO | 2005113036 A1 | 12/2005 |
| WO | 2006053007 A2 | 5/2006 |
| WO | 2007064835 A2 | 6/2007 |
| WO | 2007078937 A1 | 7/2007 |
| WO | 2008024810 A2 | 2/2008 |
| WO | 2008029403 A1 | 3/2008 |
| WO | 2008133702 A1 | 11/2008 |
| WO | 2009045462 A1 | 4/2009 |
| WO | 2009049252 A1 | 4/2009 |
| WO | 2009066287 A3 | 5/2009 |

(56) References Cited

FOREIGN PATENT DOCUMENTS

| | | | |
|---|---|---|---|
| WO | 2009066288 A1 | 5/2009 |
| WO | 2009098648 A2 | 8/2009 |
| WO | 2009134380 A2 | 11/2009 |
| WO | 2010053702 A1 | 5/2010 |
| WO | 2010132077 A1 | 11/2010 |
| WO | 2010138848 A1 | 12/2010 |
| WO | 2010147659 A2 | 12/2010 |
| WO | 2011095483 A1 | 8/2011 |
| WO | 2012045667 A2 | 4/2012 |
| WO | 2012108959 A1 | 8/2012 |
| WO | 2012134588 A1 | 10/2012 |
| WO | 2012177353 A1 | 12/2012 |
| WO | 2012178134 A2 | 12/2012 |
| WO | 20130149186 | 12/2012 |
| WO | 2013078200 A1 | 5/2013 |
| WO | 2013134486 A2 | 9/2013 |
| WO | 2013177565 A1 | 11/2013 |
| WO | 2013182321 A1 | 12/2013 |
| WO | 2014109898 A1 | 7/2014 |
| WO | 2014110538 A1 | 7/2014 |
| WO | 2014194183 A2 | 12/2014 |
| WO | 2015056259 A1 | 4/2015 |
| WO | 2015073211 A1 | 5/2015 |
| WO | 2015081337 A2 | 6/2015 |
| WO | 2015187366 A1 | 12/2015 |
| WO | 2016004088 A1 | 1/2016 |
| WO | 2016022650 A1 | 2/2016 |
| WO | 2016041873 A1 | 3/2016 |
| WO | 2016089702 A1 | 6/2016 |
| WO | 2016141082 A1 | 9/2016 |
| WO | 2016161254 A1 | 10/2016 |
| WO | 2017004278 A1 | 1/2017 |
| WO | 2017091624 A1 | 6/2017 |
| WO | 2017105600 A1 | 6/2017 |
| WO | 2017184988 A1 | 10/2017 |
| WO | 2017205816 A1 | 11/2017 |
| WO | 2018009614 A1 | 1/2018 |
| WO | 2018067748 A1 | 4/2018 |
| WO | 2018120104 A1 | 7/2018 |
| WO | 2018136799 A1 | 7/2018 |
| WO | 2018204568 A1 | 11/2018 |
| WO | 2019077482 A1 | 4/2019 |
| WO | 2019094440 A1 | 5/2019 |
| WO | 2019213493 A1 | 11/2019 |
| WO | 2019246381 A1 | 12/2019 |
| WO | 2018009614 A1 | 4/2020 |
| WO | 2020081393 A1 | 4/2020 |
| WO | 2021011738 A1 | 1/2021 |

OTHER PUBLICATIONS

Unger, Jeff, et al., "Glucose Control in the Hospitalized Patient," Emerg. Med 36(9):12-18 (2004).

Glucommander FAQ downloaded from https://adaendo.com/GlucommanderFAQ.html on Mar. 16, 2009.

Finfer, Simon & Heritier, Stephane. (2009). The NICE-SUGAR (Normoglycaemia in Intensive Care Evaluation and Survival Using Glucose Algorithm Regulation) Study: statistical analysis plan. Critical care and resuscitation : journal of the Australasian Academy of Critical Care Medicine. 11. 46-57.

Letters to the Editor regarding "Glucose Control in Critically Ill Patients," N Engl J Med 361: 1, Jul. 2, 2009.

"Medtronic is Leading a Highly Attractive Growth Market," Jun. 2, 2009.

Davidson, Paul C., et al. "Glucommander: An Adaptive, Computer-Directed System for IV Insulin Shown to be Safe, Simple, and Effective in 120,618 Hours of Operation," Atlanta Diabetes Associates presentation Nov. 16, 2003.

Davidson, Paul C., et al. "Pumpmaster and Glucommander," presented at the MiniMed Symposium, Atlanta GA, Dec. 13, 2003.

Kanji S., et al. "Reliability of point-of-care testing for glucose measurement in critically ill adults," Critical Care Med, vol. 33, No. 12, pp. 2778-2785, 2005.

Krinsley James S., "Severe hypoglycemia in critically ill patients: Risk factors and outcomes," Critical Care Med, vol. 35, No. 10, pp. 1-6, 2007.

European Patent Office, "Notification of Transmittal of the ISR and the Written Opinion of the International Searching Authority, or the Declaration," in PCT Application No. PCT/GB2015/050248, dated Jun. 23, 2015, 12 pages.

Farkas et al. ""Single-Versus Triple-Lumen Central Catheter-Related Sepsis: A Prospective Randomized Study in a Critically Ill Population"" The American Journal of Medicine September 1992 vol. 93 p. 277-282.

Davidson, Paul C., et al., A computer-directed intravenous insulin system shown to be safe, simple,and effective in 120,618 h of operation. Diabetes Care, vol. 28, No. 10, Oct. 2005, pp. 2418-2423.

International Search Report and Written Opinion for the International Patent Application No. PCT/US2021/016283, dated Jun. 2, 2021, 15 pages.

Gorke, A. "Microbial contamination of haemodialysis catheter connections." EDTNA/ERCA journal (English ed.) vol. 31,2 (2005): 79-84. doi:10.1111/j.1755-6686.2005.tb00399.x.

Lovich et al. "Central venous catheter infusions: A laboratory model shows large differences in drug delivery dynamics related to catheter dead volume" Critical Care Med 2007 vol. 35, No. 12.

Van Den Berghe, Greet, M.D., Ph.D., et al., Intensive Insulin Therapy in Critically III Patients, The New England Journal of Medicine, vol. 345, No. 19, Nov. 8, 2001, pp. 1359-1367.

Templeton et al., "Multilumen Central Venous Catheters Increase Risk for Catheter-Related Bloodstream Infection: Prospective Surveillance Study" Infection 2008; 36: 322-327.

Wilson, George S., et al., Progress toward the Development of an Implantable Sensor for Glucose, Clin. Chem., vol. 38, No. 9, 1992, pp. 1613-1617.

Yeung et al. "Infection Rate for Single Lumen v Triple Lumen Subclavian Catheters" Infection Control and Hospital Epidemiology, vol. 9, No. 4 (Apr. 1988) pp. 154-158 The University of Chicago Press.

International Search Report and Written Opinion, International Application No. PCT/US2010/033794 dated Jul. 16, 2010.

International Search Report and Written Opinion in PCT/US2008/079641 dated Feb. 25, 2009.

Berger, ""Measurement of Analytes in Human Serum and Whole Blood Samples by Near-Infrared Raman Spectroscopy,"" Ph.D. Thesis, Massachusetts Institute of Technology, Chapter 4, pp. 50-73,1998.

Berger, "An Enhanced Algorithm for Linear Multivariate Calibration," Analytical Chemistry, vol. 70, No. 3, pp. 623-627, Feb. 1, 1998.

Billman et al.,"Clinical Performance of an In line Ex-Vivo Point of Care Monitor: A Multicenter Study," Clinical Chemistry 48: 11, pp. 2030-2043, 2002.

Widness et al., "Clinical Performance on an In-Line Point-of-Care Monitor in Neonates"; Pediatrics, vol. 106, No. 3, pp. 497-504, Sep. 2000.

Finkielman et al., "Agreement Between Bedside Blood and Plasma Glucose Measurement in the ICU Setting" retrieved from http://www.chestjournal.org; CHEST/127/5/May 2005.

Glucon Critical Care Blood Glucose Monitor; Glucon; retrieved from http://www.glucon.com.

Fogt, et al., "Development and Evaluation of a Glucose Analyzer for a Glucose-Controlled Insulin Infusion System (Biostator)"; Clinical Chemistry, vol. 24, No. 8, pp. 1366-1372, 1978.

Vonach et al., "Application of Mid-Infrared Transmission Spectrometry to the Direct Determination of Glucose in Whole Blood," Applied Spectroscopy, vol. 52, No. 6, 1998, pp. 820-822.

Muniyappa et al., "Current Approaches for assessing insulin sensitivity and resistance in vivo: advantages, limitations, and appropriate usage," AJP-Endocrinol Metab, vol. 294, E15-E26, first published Oct. 23, 2007.

R Anthony Shaw, et al., "Infrared Spectroscopy in Clinical and Dianostic Analysis," Encyclopedia of Analytical Chemistry, ed. Robert A. Meyers, John Wiley & Sons, Ltd., pp. 1-20, 2000.

(56) References Cited

OTHER PUBLICATIONS

International Preliminary Report on Patentability for the International Patent Application No. PCT/US2019/053603, dated Apr. 8, 2021, 9 pages.

International Search Report and Written Opinion for the International Patent Application No. PCT/US2019/053603, dated Jan. 7, 2020, 16 pages.

Dassau et al., "Detection of a meal using continuous glucose monitoring: Implications for an artificial [beta]-cell." Diabetes Care, American Diabetes Association, Alexandria, VA, US, 31(2):295-300 (2008).

Cameron et al., "Probabilistic Evolving Meal Detection and Estimation of Meal Total Glucose Appearance Author Affiliations", J Diabetes Sci and Tech.Vol., Diabetes Technology Society ;(5):1022-1030 (2009).

Lee et al., "A closed-loop artificial pancreas based on model predictive control: Human-friendly identification and automatic meal disturbance rejection", Biomedical Signal Processing and Control, Elsevier, Amsterdam, NL, 4 (4):1746-8094 (2009).

An Emilia Fushimi: "Artificial Pancreas: Evaluating the ARG Algorithm Without Meal Announcement", Journal of Diabetes Science and Technology Diabetes Technology Society, Mar. 22, 2019, pp. 1025-1043.

International Search Report and Written Opinion for the International Patent Application No. PCT/US2021/017441, dated May 25, 2021, 12 pages.

International Search Report and Written Opinion for the InternationalPatent Application No. PCT/US2021/017664, dated May 26, 2021, 16 pages.

Mirko Messori et al: "Individualized model predictive control for the artificial pancreas: In silico evaluation of closed-loop glucose control", IEEE Control Systems, vol. 38, No. 1, Feb. 1, 2018, pp. 86-104.

International Search Report and Written Opinion for the International Patent Application No. PCT/US2021/017662, dated May 26, 2021, 14 pages.

Anonymous: "Reservoir Best Practice and Top Tips" Feb. 7, 2016, URL: https://www.medtronic-diabetes.co.uk/blog/reservoir-best-practice-and-top-tips, p. 1.

Gildon Bradford: "InPen Smart Insulin Pen System: Product Review and User Experience" Diabetes Spectrum, vol. 31, No. 4, Nov. 15, 2018, pp. 354-358.

International Search Report and Written Opinion for the International Patent Application No. PCT/US2021/016050, dated May 27, 2021, 16 pages.

International Search Report and Written Opinion for the International Patent Application No. PCT/US2020/065226, dated May 31, 2021, 18 pages.

International Search Report and Written Opinion for the International Patent Application No. PCT/US2021/017659, dated May 31, 2021, 13 pages.

Montaser Eslam et al., "Seasonal Local Models for Glucose Prediction in Type 1 Diabetes", IEE Journal of Biomedical and Health Informatics, IEEE, Piscataway, NJ, USA, vol. 24, No. 7, Jul. 2020, pp. 2064-2072.

Samadi Sediqeh et al., "Meal Detection and Carbohydrate Estimation Using Continuous Glucose Sensor Data" IEEE Journal of Biomedical and Health Informatics, IEEE, Piscataway, NJ, USA, vol. 21, No. 3, May 1, 2017, pp. 619-627.

Samadi Sediqeh et al., "Automatic Detection and Estimation of Unannouced Meals for Multivariable Artificial Pancreas System", Diabetis Technology & Therapeutics, vol. 20m No. 3, Mar. 1, 2018, pp. 235-246.

European Search Report for the European Patent Application No. 21168591.2, dated Oct. 13, 2021, 151 pages.

International Search Report and Written Opinion for the International Patent Application No. PCT/US2021/041954, dated Oct. 25, 2021, 13 pages.

International Search Report and Written Opinion for the International Patent Application No. PCT/US2021/047771, dated Dec. 22, 2021, 11 pages.

International Search Report and Written Opinion for the International Patent Application No. PCT/US2021/052855, dated Dec. 22, 2021, 11 pages.

International Search Report and Written Opinion for the International Patent Application No. PCT/US2020/050332, dated Sep. 12, 2020, 12 pages.

International Search Report and Written Opinion for Application No. PCT/US2019/030562, dated Sep. 25, 2019, 19 pages.

Khodaei et al., "Physiological Closed-Loop Contol (PCLC) Systems: Review of a Modern Frontier in Automation", IEEE Access, IEEE, USA, vol. 8, Jan. 20, 2020, pp. 23965-24005.

E. Atlas et al., "MD-Logic Artificial Pancreas System: A pilot study in adults with type 1 diabetes", Diabetes Care, vol. 33, No. 5, Feb. 11, 2010, pp. 1071-1076.

Anonymous: "Fuzzy control system", Wikipedia, Jan. 10, 2020. URL: https://en.wikipedia.org/w/index.php?title=Fuzzy_control_system&oldid=935091190.

International Search Report and Written Opinion for the International Patent Application No. PCT/US2021/022694, dated Jun. 25, 2021, 13 pages.

International Search Report and Written Opinion for International Patent Application No. PCT/US2021/051027, dated Jan. 7, 2022, 16 pages.

International Search Report and Written Opinion for International Patent Application No. PCT/US2021/052372, dated Jan. 26, 2022, 15 pages.

International Search Report and Written Opinion for the International Patent Application No. PCT/US2021/046607, dated Jan. 31, 2022, 20 pages.

International Search Report and Written Opinion for the International Patent Application No. PCT/US2021/055745, dated Feb. 14, 2022, 13 pages.

Anonymous: "Artificial pancreas—Wikipedia", Mar. 13, 2018 (Mar. 13, 2018), XP055603712, Retrieved from the Internet: URL: https://en.wikipedia.org/w/index php?title-Artificial pancreas&oldid=830262114#cite_note-9 [retrieved on Jul. 9, 2019] section "Medical Equipment" and the figure labeled "The medical equipment approach to an artifical pancreas".

Kaveh et al., "Blood Glucose Regulation via Double Loop Higher Order Sliding Mode Control and Multiple Sampling Rate." Paper presented at the proceedings of the 17th IFAC World Congress, Seoul, Korea (Jul. 2008).

Dassau et al., "Real-Time Hypoglycemia Prediction Suite Using Contineous Glucose Monitoring," Diabetes Care, vol. 33, No. 6, 1249-1254 (2010).

International Search Report and Written Opinon for International application No. PCT/US17/53262, dated Dec. 13, 2017 8 pages.

Van Heusden, K. et al., "Control-Relevant Models for Glucose Control using A Priori Patient Characteristics", IEEE Transactions on Biomedical Engineering, vol. 59, No. 7, (Jul. 1, 2012) pp. 1839-1849.

Doyle III, et al., "Run-to-Run Control Strategy for Diabetes Management." Paper presented at 23rd Annual International Conference of the IEEE Engineering in Medicine and Biology Society, Istanbul, Turkey (Oct. 2001).

Bequette, B.W., and Desemone, J., "Intelligent Dosing Systems": Need for Design and Analysis Based on Control Theory, Diabetes Technology and Therapeutics 9(6): 868-873 (2004).

Parker, R.S., et al., "A Model-Based Agorithm for Blood Gucose Control in Type 1 Diabetic Patients." IEEE Transactions on Biomedical Engineering, 46 (2) 148-147 (1999).

International Search Report and Written Opinion for the Application No. PCT/US2017/015601, dated May 16, 2017, 12 pages.

International Search Report and Written Opinion for the Application No. PCT/US2018/018901, dated Aug. 6, 2018, 12 pages.

International Search Report and Written Opinion for Application No. PCT/US2018/052467, dated Jan. 4, 2019, 13 pages.

How to Create a QR Code that Deep Links to Your Mobile App, Pure Oxygen Labs, web<https://pureoxygenlabs.com/how-to-create-a-qr-codes-that-deep-link-to-your-mobile-app/>. Year:2017.

(56) References Cited

OTHER PUBLICATIONS

Read NFC Tags with an iPHone App on iOS 11, GoToTags, Sep. 11, 2017, web <https://gototags.com/blog/read-nfc-tags-with-an-iphone-app-on-ios-11/>. (Year:2017).

International Search Report and Written Opinion for International Application No. PCT/US2016/063350, dated Mar. 27, 2017, 9 pages.

Extended Search Report dated Aug. 13, 2018, issued in European Patent Application No. 16753053.4, 9 pages.

International Search Report and Written Opinion dated Apr. 29, 2015, received in corresponding PCT Application No. PCT/US16/18452, 9 pages.

International Preliminary Report on Patentability dated Aug. 31, 2017, issued in PCT Patent Application No. PCT/US2016/018452, 7 pages.

International Search Report and Written Opinion for the International Patent Application No. PCT/US2019/055862, dated Mar. 11, 2020.

International Search Report and Written Opinion for the International Patent Application No. PCT/US2020/052125, dated Aug. 12, 2020, 15 pages.

International Search Report and Written Opinion for the International Patent Application No. PCT/US2022/013470, dated May 6, 2022, 14 pages.

International Search Report and Written Opinion for the International Patent Application No. PCT/US2022/013473, dated May 6, 2022, 13 pages.

International Search Report and Written Opinion for the International Patent Application No. PCT/US2022/019079, dated Jun. 2, 2022, 14 pages.

International Search Report and Written Opinion for the International Patent Application No. PCT/US2022/018453, dated Jun. 2, 2022, 13 pages.

International Search Report and Written Opinion for the International Patent Application No. PCT/US22/018700, dated Jun. 7, 2022, 13 pages.

International Search Report and Written Opinion for the International Patent Application No. PCT/US22/019080, dated Jun. 7, 2022, 14 pages.

International Search Report and Written Opinion for the International Patent Application No. PCT/US22/019664, dated Jun. 7, 2022, 14 pages.

International Search Report and Written Opinion for the International Patent Application No. PCT/US21/060618, dated Mar. 21, 2022, 15 pages.

Herrero Pau et al: "Enhancing automatic closed-loop glucose control in type 1 diabetes with an adaptive meal polus calculator—in silicoevaluation under intra-day variability", Computer Methods and Programs in Biomedicine, Elsevier, Amsterdam, NL, vol. 146, Jun. 1, 2017 (Jun. 1, 2017), pp. 125-131, XP085115607, ISSN: 0169-2607, DOI:10.1016/J.CMPB.2017.05.010.

Marie Aude Qemerais: "Preliminary Evaluation of a New Semi-Closed-Loop Insulin Therapy System over the prandial period in Adult Patients with type I diabetes: the WP6. 0 Diabeloop Study", Journal of Diabetes Science and Technology Diabetes Technology Society Reprintsand permissions, Jan. 1, 2014, p. 1177-1184, Retrieved from the Internet: URL:http://journals.sagepub.com/doi/pdf/10.1177/1932296814545668 [retrieved on Jun. 6, 2022] chapter "Functioning of the Algorithm" chapter "Statistical Analysis" p. 1183, left-hand col. line 16-line 23.

Anonymous: "Kernel density estimation", Wikipedia, Nov. 13, 2020 (Nov. 13, 2020), pp. 1-12, XP055895569, Retrieved from the Internet: URL:https://en.wikipedia.org/w/index.php?title=Kernel_density_estimation&oldid=988508333 [retrieved on Jun. 6, 2022].

Anonymous: "openaps / oref0 /lib/determine-basal-js", openaps repository, Nov. 9, 2019 (Nov. 9, 2019), pp. 1-17, XP055900283, Retrieved from the Internet: URL:https://github.com/openaps/oref0/blob/master/lib/determine-basal/determine-basal.js [retrieved on Jun. 6, 2022] line 116-line 118, line 439-line 446.

Anonymous: "AndroidAPS screens", AndroidAPS documentation, Oct. 4, 2020 (Oct. 4, 2020), pp. 1-12, XP055894824, Retrieved from the Internet: URL:https://github.com/openaps/AndroidAPSdocs/blob/2508acf8b28262b411b34f416f173ac0814d7e14/docs/EN/Getting-Started/Screenshots.md [retrieved on Jun. 6, 2022].

Kozak Milos et al.: "Issue #2473 of AndroidAPS", MilosKozak / AndroidAPS Public repository, Mar. 4, 2020 (Mar. 4, 2020), pp. 1-4, XP055900328, Retrieved from the Internet: URL:https://github.com/MilosKozak/AndroidAPS/Issues/2473 [retrieved on Jun. 6, 2022].

Medication Bar Code System Implementation Planning Section I: A Bar Code Primer for Leaders, Aug. 2013.

Medication Bar Code System Implementation Planning Section II: Building the Case for Automated Identification of Medications, Aug. 2013.

Villareal et al. (2009) in: Distr. Comp. Art. Intell. Bioninf. Soft Comp. Amb. Ass. Living; Int. Work Conf. Art. Neural Networks (IWANN) 2009, Lect. Notes Comp. Sci. vol. 5518; S. Omatu et al. (Eds.), pp. 870-877.

Fox, Ian G.; Machine Learning for Physiological Time Series: Representing and Controlling Blood Glucose for Diabetes Management; University of Michigan. ProQuest Dissertations Publishing, 2020. 28240142. (Year: 2020).

International Search Report and Written Opinion for the International Patent Application No. PCT/US2022/012896, dated Apr. 22, 2022, 15 pages.

\* cited by examiner

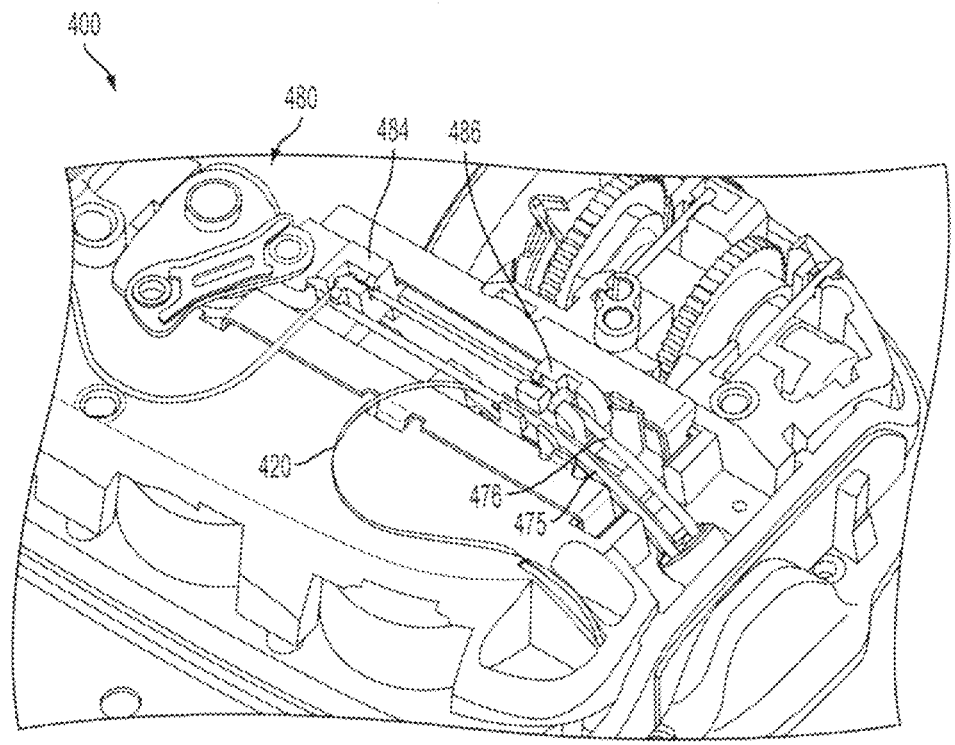
FIG. 39
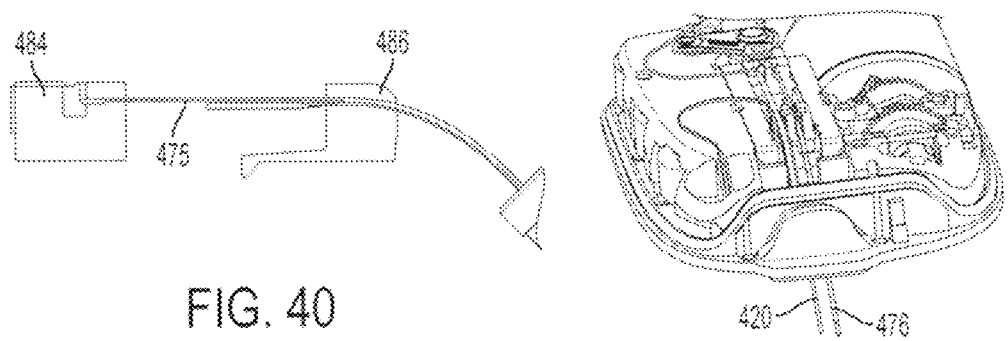
FIG. 40
FIG. 41

FLUID DELIVERY AND INFUSION DEVICES, AND METHODS OF USE THEREOF

CROSS REFERENCE TO RELATED APPLICATIONS

This application is a continuation of U.S. application Ser. No. 15/047,028, filed Feb. 18, 2016, which claims the benefit of U.S. Provisional Application No. 62/117,937, filed Feb. 18, 2015, which are hereby incorporated by reference in their entirety.

TECHNICAL FIELD

The present invention relates to medical devices, such as fluid delivery devices for delivering therapeutic liquids to a patient, and more particularly, to an infusion pump for delivering therapeutic liquids to a patient.

BACKGROUND INFORMATION

Fluid delivery devices have numerous uses such as delivering a liquid medicine or other therapeutic fluid to a patient subcutaneously. In a patient with diabetes mellitus, for example, ambulatory infusion pumps have been used to deliver insulin to a patient. These ambulatory infusion pumps have the ability to offer sophisticated fluid delivery profiles including variable basal rates and bolus requirements. The ability to carefully control drug delivery can result in better efficacy of the drug and therapy and less toxicity to the patient.

Some existing ambulatory infusion pumps include a reservoir to contain the liquid medicine and use electromechanical pumping or metering technology to deliver the liquid medicine via tubing to a needle and/or soft cannula that is inserted subcutaneously into the patient. These existing devices allow control and programming via electromechanical buttons or switches located on the housing of the device. The devices include visual feedback via text or graphic screens and may include alert or warning lights and audio or vibration signals and alarms. Such devices are typically worn in a harness or pocket or strapped to the body of the patient.

Some infusion pumps have been designed to be relatively small, low cost, light-weight, and easy-to-use. One example of such a pump is the OMNIPOD® insulin infusion pump available from Insulet Corporation. Examples of infusion pumps are also described in greater detail, for example, in U.S. Pat. Nos. 7,128,727; 7,018,360; and 7,144,384 and U.S. Patent Application Publication Nos. 2007/0118405, 2006/0282290, 2005/0238507, and 2004/0010207, which are fully incorporated herein by reference. These pumps include insertion mechanisms for causing a transcutaneous access tool, such as a needle and/or soft cannula, to be inserted into a patient. Although such pumps are effective and provide significant advantages over other insulin infusion pumps, the design of the insertion mechanism may be improved, for example, to reduce the size of the pump and/or to improve the comfort to the user. These pumps also include fluid driving mechanisms for driving fluid from a reservoir through the transcutaneous access tool. The fluid driving mechanisms may also be improved to facilitate assembly and use of the pump.

SUMMARY

The present disclosure provides various fluid delivery devices to deliver a liquid medicine or other therapeutic fluid to a patient subcutaneously.

In certain embodiments, the fluid delivery device may comprise an ambulatory infusion device to administer a liquid medicine or other therapeutic fluid to a patient. The fluid delivery device may include one or more batteries for providing a power source, a fluid reservoir for holding a fluid, a fluid drive mechanism for driving the fluid out of the reservoir, a fluid passage mechanism for receiving the fluid from the reservoir and passing the fluid to a destination via a transcutaneous access tool, and a transcutaneous access tool insertion mechanism for deploying the transcutaneous access tool.

In certain embodiments, an infusion device may comprise a fluid reservoir for containing a therapeutic fluid; and a transcutaneous access tool fluidly coupled to the fluid reservoir, which may deliver the therapeutic fluid subcutaneously and introduce a monitoring test strip subcutaneously.

In certain embodiments, a method to treat a patient may be provided comprising providing an infusion device with integrated monitoring, with the device comprising a fluid reservoir for containing a therapeutic fluid; and a transcutaneous access tool fluidly coupled to the fluid reservoir, which may deliver the therapeutic fluid subcutaneously and introduce a monitoring test strip subcutaneously; delivering the therapeutic fluid subcutaneously with the transcutaneous access tool to a patient, and introducing the monitoring test strip subcutaneously with the transcutaneous access tool to the patient.

In certain embodiments, the transcutaneous access tool includes a needle/trocar, and the transcutaneous access tool insertion mechanism is configured to insert and retract the needle/trocar in a single, uninterrupted motion. In such a manner, the pain of insertion and retraction of the needle/trocar experienced by the patient may be reduced.

In certain embodiments, the fluid delivery device may comprise a fluid reservoir; a transcutaneous access tool fluidly coupled to the fluid reservoir, the transcutaneous access tool including a needle/trocar; and a transcutaneous access tool insertion mechanism for deploying the transcutaneous access tool, wherein the insertion mechanism is configured to insert and retract the needle/trocar in a single, uninterrupted motion.

In certain embodiments, the fluid delivery device may comprise a fluid reservoir; a transcutaneous access tool fluidly coupled to the fluid reservoir, the transcutaneous access tool including at least a needle/trocar; and a transcutaneous access tool insertion mechanism for deploying the transcutaneous access tool, wherein the insertion mechanism is configured to insert the needle/trocar with an increasing insertion force as the needle/trocar moves in an insertion direction.

In certain embodiments, the transcutaneous access tool insertion mechanism for deploying a transcutaneous access tool including a cannula and a needle/trocar located inside of the cannula may comprise a first sliding member configured to move the needle/trocar in an insertion direction and a retraction direction; a second sliding member configured to move the cannula in the insertion direction; a torsion spring; and linkages coupled between the torsion spring and the first sliding member such that energy stored in the torsion spring causes the linkages to move the first sliding member in the insertion direction and the retraction direction.

In certain embodiments, the drive mechanism may comprise a clutch mechanism. As explained herein, by using a clutch mechanism, the number of fluid path prime pulses to prime the pump may be reduced and a full and proper priming of the fluid path before placement on the body may be better assured. The clutch mechanism may also be made suitable for other drug applications without significant redesign, and be more easily inspected than conventional drive mechanisms for infusion devices.

In certain embodiments, the fluid delivery device may comprise a fluid reservoir; a transcutaneous access tool fluidly coupled to the fluid reservoir; and a drive mechanism for driving fluid from the reservoir. The drive mechanism may comprise a plunger received in the reservoir; a leadscrew extending from the plunger; a nut threadably engaged with the leadscrew; a drive wheel; and a clutch mechanism coupled to the drive wheel, wherein the clutch mechanism is configured to allow the nut to pass through the clutch mechanism when disengaged and is configured to grip the nut when engaged such that the drive wheel rotates the nut to advance the leadscrew and the plunger into the reservoir.

In certain embodiments, the fluid delivery device may comprise a fluid reservoir; a transcutaneous access tool fluidly coupled to the fluid reservoir; and a drive mechanism for driving fluid from the reservoir The drive mechanism may comprise a plunger received in the reservoir; an elongated assembly comprising a first elongated member and a second elongated member; the first elongated member extending from the plunger; the second elongated member coupled to the first elongated member; a drive wheel; and a clutch mechanism coupled to the drive wheel, wherein the clutch mechanism is configured to allow the second elongated member to pass through when disengaged and is configured to grip the second elongated member when engaged such that the drive wheel rotates the second elongated member to advance the first elongated member and the plunger into the reservoir.

In certain embodiments, a method of operating a foregoing fluid delivery device may comprise providing the fluid delivery device; holding the clutch mechanism in a disengaged position; filling the fluid reservoir with fluid; passing the second elongated member through the clutch mechanism such that the plunger is retracted within the reservoir; releasing the clutch mechanism from the disengaged position; and engaging the clutch mechanism with the second elongated member.

In certain embodiments, present disclosure provides a medical device comprising an infusion device comprising a fluid reservoir to contain a therapeutic fluid and a transcutaneous access tool fluidly coupled to the fluid reservoir, the transcutaneous access tool configured to deliver the therapeutic fluid subcutaneously to a patient; wherein the infusion device operates in a stand-by mode prior to the therapeutic fluid being introduced into the fluid reservoir; wherein the infusion device operates to deploy the transcutaneous access tool within a predetermined deployment time period upon filling the fluid reservoir to a predetermined fill level with the therapeutic fluid.

In certain embodiments, the predetermined deployment time period may be greater than or equal to 30 seconds, and/or the predetermined deployment time period may be less than or equal to 15 minutes. In other embodiments, the transcutaneous access tool introduction time period may be greater than or equal to 1 minute, and/or less than or equal to 10 minutes. In other embodiments, the transcutaneous access tool introduction time period may be greater than or equal to 2 minutes, and/or less than or equal to 5 minutes.

In certain embodiments, the infusion device may comprise a non-transitory memory including stored instructions that, when executed by at least one processor, cause the infusion device to deploy the transcutaneous access tool within the predetermined deployment time period.

In certain embodiments, the infusion device may comprise at least one sensor, wherein the at least one sensor may operate by sending an input signal to the at least one processor when the therapeutic fluid in the fluid reservoir reaches the predetermined fill level.

In certain embodiments, the at least one processor may operate by detecting the input signal from the at least one sensor, and upon detecting the input signal from the at least one sensor, the at least one processor may operate to execute the instructions that cause the infusion device to deploy the transcutaneous access tool within the predetermined deployment time period.

In certain embodiments, the infusion device may operate to deliver the therapeutic fluid in the fluid reservoir through the transcutaneous access tool after a predetermined infusion delay time period. The infusion device may operate to initiate the predetermined infusion delay time period when the transcutaneous access tool is deployed. The predetermined infusion delay time period may be at least 1 hour, at least 8 hours, at least 16 hours or at least 20 hours.

In certain embodiments, a method of treating a patient is provided, comprising introducing a therapeutic fluid to an infusion device, wherein the infusion device comprises a fluid reservoir which contains the therapeutic fluid, and a transcutaneous access tool fluidly coupled to the fluid reservoir, the transcutaneous access tool to deliver the therapeutic fluid subcutaneously to the patient; securing the infusion device to the patient; introducing the transcutaneous access tool into the patient; delivering the therapeutic fluid subcutaneously to a patient with the transcutaneous access tool; and wherein the infusion device introduces the transcutaneous access tool into the patient within a transcutaneous access tool introduction time period after introducing a therapeutic fluid to the infusion device, wherein the transcutaneous access tool introduction time period is greater than or equal to 30 seconds, and less than or equal to 15 minutes.

In certain embodiments, the infusion device may comprise a non-transitory memory configured to store instructions that, when executed by at least one processor, cause the infusion device to introduce the transcutaneous access tool into the patient within the transcutaneous access tool introduction time period after the therapeutic fluid is introduced to the infusion device.

In certain embodiments, the infusion device may comprise a sensor which sends an input signal detected by the at least one processor when the fluid contained in the fluid reservoir reaches a predetermined level.

In certain embodiments, the input signal from the sensor may cause the at least one processor to execute the instructions that cause the infusion device to introduce the transcutaneous access tool into the patient within the transcutaneous access tool introduction time period after the therapeutic fluid is introduced to the infusion device.

In certain embodiments, the transcutaneous access tool introduction time period may be greater than or equal to 1 minute, and/or less than or equal to 10 minutes. In certain embodiments, the transcutaneous access tool introduction time period may be greater than or equal to 2 minutes, and/or less than or equal to 5 minutes.

In certain embodiments, the infusion device may deliver the therapeutic fluid subcutaneously to a patient with the transcutaneous access tool after an infusion delay time period which is initiated when the transcutaneous access tool is introduced into the patient, wherein the predetermined time period is at least 1 hour. In certain embodiments, the infusion delay time period may be at least 8 hours, at least 16 hours or at least 20 hours.

BRIEF DESCRIPTION OF THE DRAWINGS

These and other features and advantages will be better understood by reading the following detailed description, taken together with the drawings wherein:

FIGS. 35-41 are views of another embodiment of a fluid delivery device including an oval trocar for inserting a monitor test strip transcutaneously;

DETAILED DESCRIPTION

Figure 1:
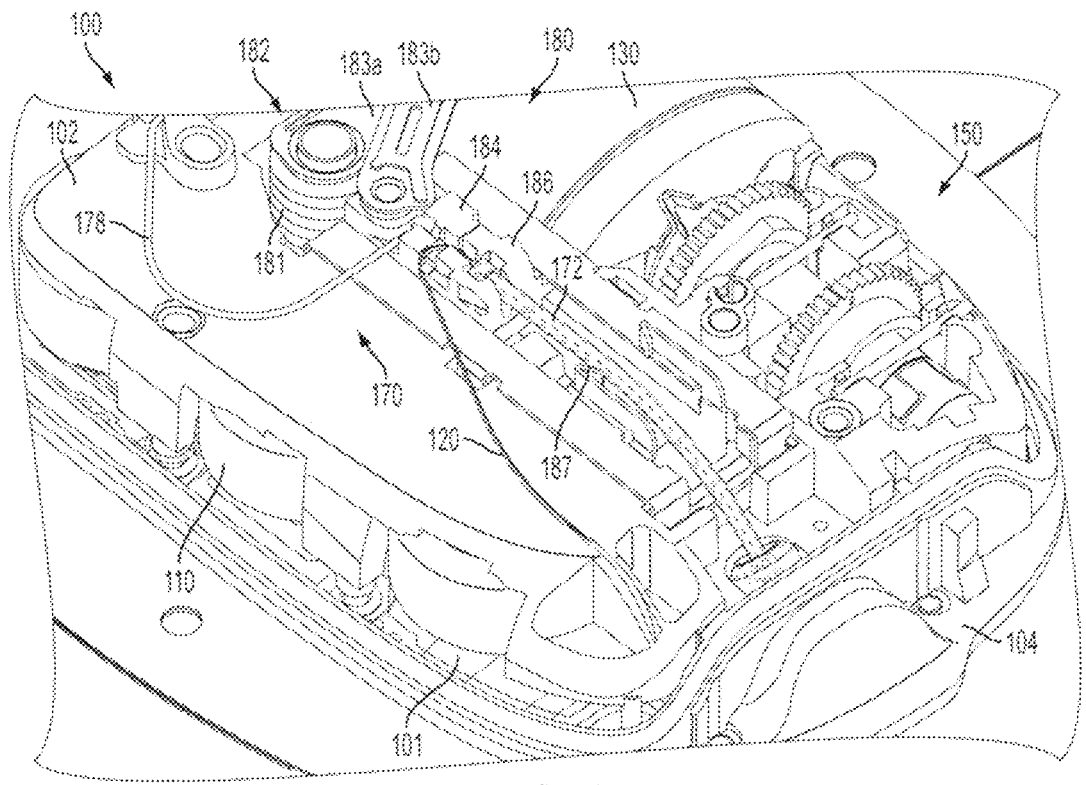
FIG. 1 is a top perspective view of a fluid delivery device with a transcutaneous access tool insertion mechanism in a pre-deployment position, consistent with the present disclosure.
Figure 2:
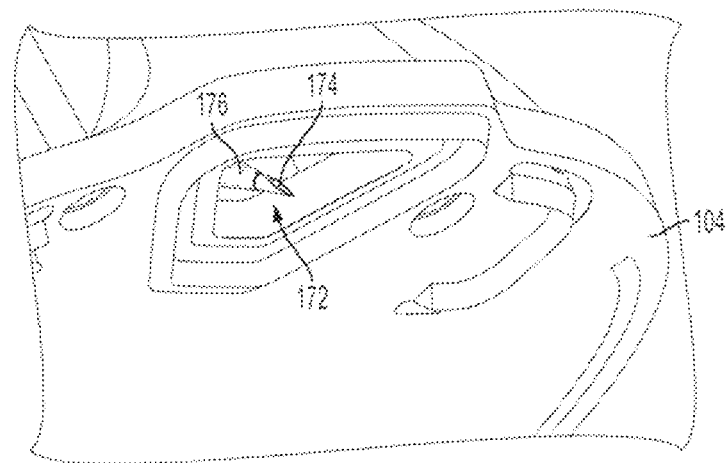
FIG. 2 is a bottom perspective view of a needle and cannula retracted into the fluid delivery device in the pre-deployment position shown in FIG. 1.
Figures 3, 4:
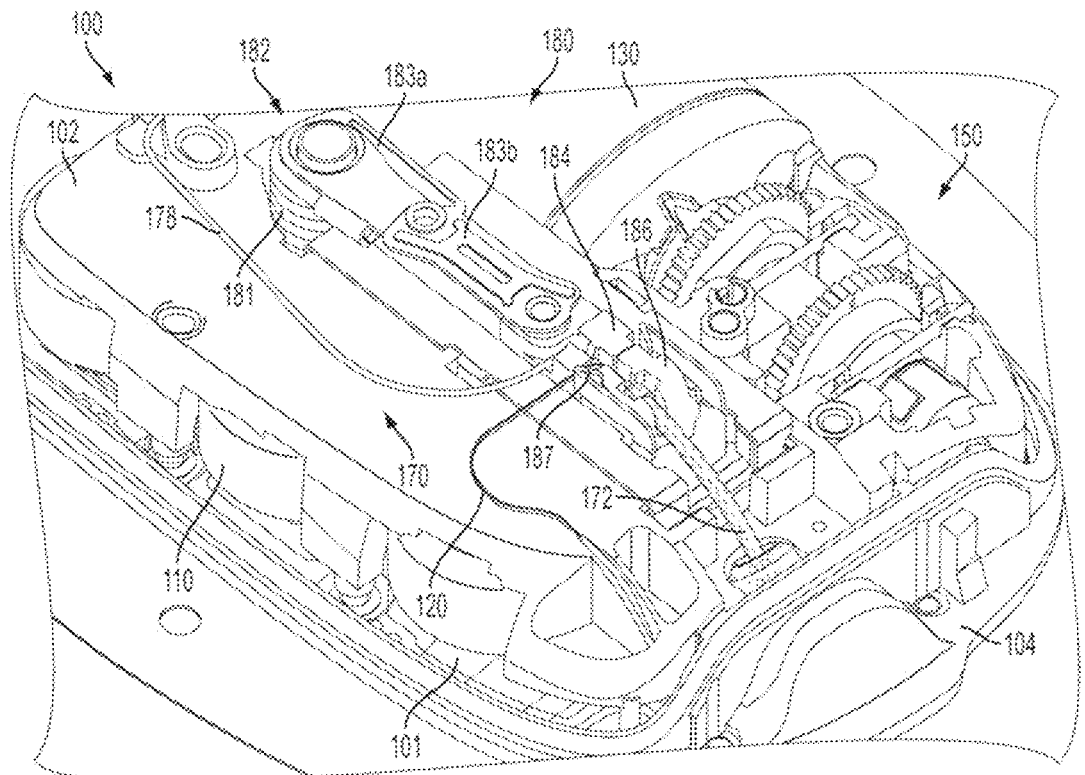
FIG. 3 is a top perspective view of the fluid delivery device shown in FIG. 1 with the insertion mechanism in an intermediate position.
FIG. 4 is a bottom perspective view of the needle and cannula extending from the fluid delivery device in the intermediate position shown in FIG. 3.

A fluid delivery device, consistent with embodiments of the present disclosure, may be used to deliver a therapeutic fluid (e.g. a liquid medicine) to a patient via a transcutaneous access tool, such as a needle/trocar and/or a cannula. A transcutaneous access tool insertion mechanism may be used to deploy the transcutaneous access tool, for example, by inserting and retracting a needle/trocar in a single, uninterrupted motion. The insertion mechanism may also provide an increasing insertion force as the needle/trocar moves in the insertion direction. The fluid delivery device may also include a clutch mechanism to facilitate filling a reservoir and engagement of a drive mechanism for driving fluid out of the reservoir. In certain embodiments, the fluid delivery device may comprise an ambulatory infusion device.

In other embodiments, a fluid delivery device may be used to deliver a therapeutic fluid to a patient with integrated monitoring. In these embodiments, the fluid deliver device may include a transcutaneous access tool configured to introduce a monitoring test strip through the skin of the patient, for example, using one or more needles, cannulas and/or trocars.

Referring to FIGS. 1-6, one embodiment of a fluid delivery device 100 is shown and described. In the exemplary embodiment, the fluid delivery device 100 is used to subcutaneously deliver a fluid, such as a liquid medicine to a person or an animal. Those skilled in the art will recognize that the fluid delivery device 100 may be used to deliver other types of fluids. The fluid delivery device 100 may be used to deliver fluids in a controlled manner, for example, according to fluid delivery profiles accomplishing bolus requirements, continuous infusion and variable flow rate delivery.

According to one embodiment, the fluid delivery device 100 may include one or more batteries 110 for providing a power source, a fluid reservoir 130 for holding a fluid, a fluid drive mechanism 150 for driving the fluid out of the reservoir 130, a fluid passage mechanism 170 for receiving the fluid from the reservoir 130 and passing the fluid to a destination via a transcutaneous access tool 172, and a transcutaneous access tool insertion mechanism 180 for deploying the transcutaneous access tool 172. The fluid delivery device 100 may include a circuit board 101 with control circuitry for controlling the device and a chassis 102 that provides mechanical and/or electrical connections between components of the fluid deliver device 100. The fluid delivery device 100 may also include a housing 104 to enclose the circuit board 101, the chassis 102, and the components 110, 130, 150, 170, 180.

The fluid delivery device 100 may also include integrated monitoring. A monitor test strip 120 coupled to a monitor (not shown) in the device 100 may be introduced by the transcutaneous access tool 172 subcutaneously. The fluid delivery device 100 may be configured to receive data from the monitoring test strip concerning one or more physiologic conditions of the patient. For example, the fluid delivery device 100 may be configured to receive data from the monitoring test strip concerning a glucose level of the patient, and determining an output of a fluid such as insulin from the reservoir based on the glucose level. One example of the monitor test strip is a CGM test strip (such as the type available from Nova Biomedical) which may be understood as a glucose sensor configured to test for a concentration level of glucose in the blood of a patient.

The transcutaneous access tool 172 includes an introducer trocar or needle 174 at least partially positioned within a lumen 175 of a cannula 176 (e.g., a soft flexible cannula), which is capable of passing the fluid into the patient. In particular, the introducer needle/trocar 174 may initially penetrate the skin such that both the introducer needle/trocar 174 and the cannula 176 are introduced (inserted) into the patient, and the introducer needle/trocar 174 may then be retracted within the cannula 176 such that the cannula 176 remains inserted. A fluid path, such as tubing 178, fluidly couples the reservoir 130 to the lumen 175 of cannula 176 of the transcutaneous access tool 172. The transcutaneous access tool 172 may also be used to introduce a monitoring test strip subcutaneously into the patient for monitoring purposes, as described in greater detail below.

Figure 5:
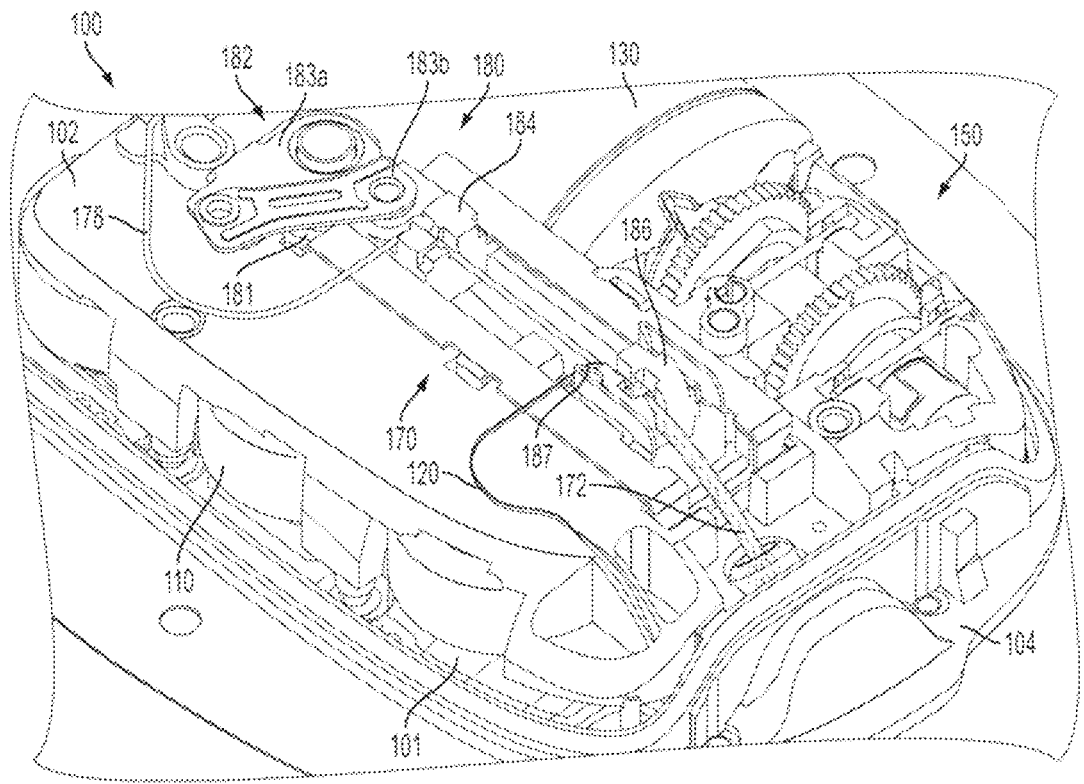
FIG. 5 is a top perspective view of the fluid delivery device shown in FIG. 1 with the insertion mechanism in a post-deployment position.
Figure 6:
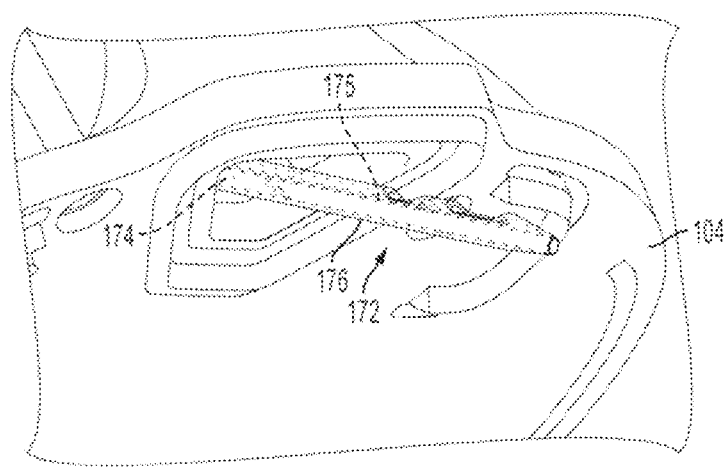
FIG. 6 is a bottom perspective view of the cannula extending from the fluid delivery device in the post-deployment position shown in FIG. 5.

The transcutaneous access tool insertion mechanism 180 is coupled to the transcutaneous access tool 172 to deploy the transcutaneous access tool 172, for example, by inserting the needle/trocar 174 and cannula 176 through the skin of a patient and retracting the needle/trocar 174. In the illustrated embodiment, the insertion mechanism 180 includes a spring-biased linkage mechanism 182 and sliding members 184, 186 coupled to the needle/trocar 174 and cannula 176, respectively, for moving the needle/trocar 174 and cannula 176 in the insertion direction and for moving the needle/trocar 174 in the retraction direction. In a single, uninterrupted motion, the spring-biased linkage mechanism 182 moves from a pre-deployment position (FIG. 1) with both needle/trocar 174 and cannula 176 retracted (FIG. 2) to an intermediate position (FIG. 3) with both needle/trocar 174 and cannula 176 inserted (FIG. 4) to a post-deployment position (FIG. 5) with the needle/trocar 174 retracted and the cannula 176 inserted (FIG. 6).

One embodiment of the spring-biased linkage mechanism 182 includes a helical torsion spring 181 and first and second linkages 183a, 183b coupled between the torsion spring 181 and the first sliding member 184. Energy stored in the torsion spring 181 applies a force to the linkages 183a, 183b, which applies a force to the first sliding member 184 to move the first sliding member 184 in both the insertion direction and in the retraction direction. In the pre-deployment position (FIG. 1), the torsion spring 181 is loaded and the sliding members 184, 186 are locked and prevented from moving. When the sliding members 184, 186 are released, the energy stored in the torsion spring 181 causes the first linkage 183a to rotate (e.g., clockwise as shown), which applies a force to the first sliding member 184 through the second linkage 183b causing the first sliding member 184 with the needle/trocar 174 to move (with the second sliding member 186) in the insertion direction. In the intermediate position (FIG. 3), the linkages 183a, 183b are fully extended with the needle/trocar 174 and cannula 176 being inserted, the second sliding member 186 is locked, and the remaining energy stored in the torsion spring 181 causes the first linkage 183a to continue to rotate, which applies an opposite force to the first sliding member 184 through the second linkage 183b causing the first sliding member 184 with the needle/trocar 174 to move in the retraction direction to the post-deployment position (FIG. 5). In the illustrated embodiment, the second sliding member 186 is locked against retraction by one or more latches 187. Thus, in the foregoing manner, the continuous uninterrupted clockwise rotation of first linkage 183a via the energy of torsion spring 181 provides the transcutaneous access tool insertion mechanism 180 with the ability to insert and retract the needle/trocar 174 in a single, uninterrupted motion.

The spring-biased linkage mechanism 182 allows a single spring and motion to achieve both the insertion and retraction and has a relatively small size. The spring-biased linkage mechanism 182 also reduces the static stresses caused by locking and holding back the sliding members 184, 186 and provides a smoother and more comfortable needle/trocar insertion because of the way the linkages 183a, 183b vector the forces applied to the sliding members 184, 186. The static forces on the sliding members 184, 186 are relatively small in the pre-deployment position when the linkages 183a, 183b are fully retracted. When the deployment starts and the linkages 183a, 183b start to become extended, the insertion forces increase because the force vectors increase in the insertion direction as the linkages extend 183a, 183b until a maximum insertion force is reached at the fully extended, intermediate position. By gradually increasing the insertion forces, the needle/trocar insertion and retraction is smoother, quieter and less painful.

Figure 7:
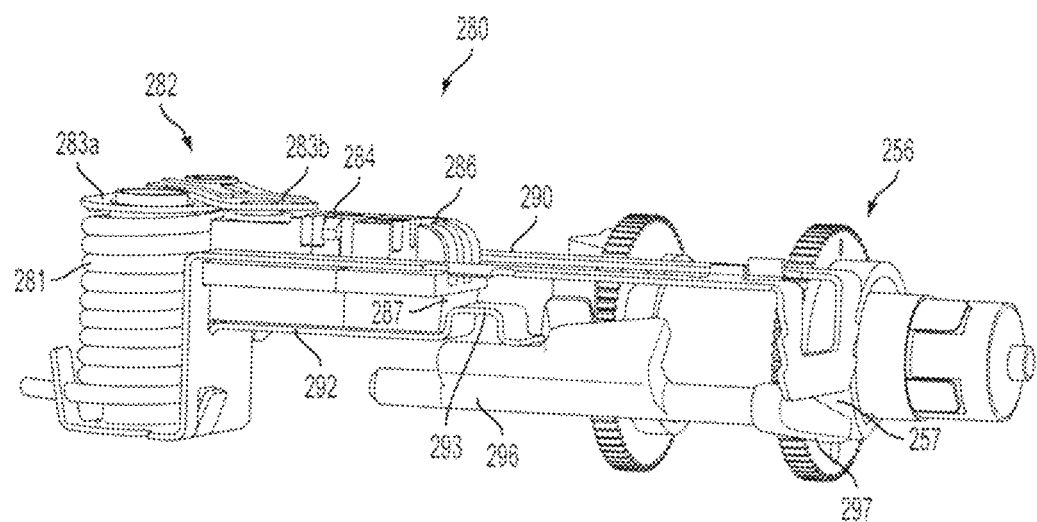
FIG. 7 is a side perspective view of another embodiment of the insertion mechanism, consistent with the present disclosure, in a pre-deployment position.
Figure 8:
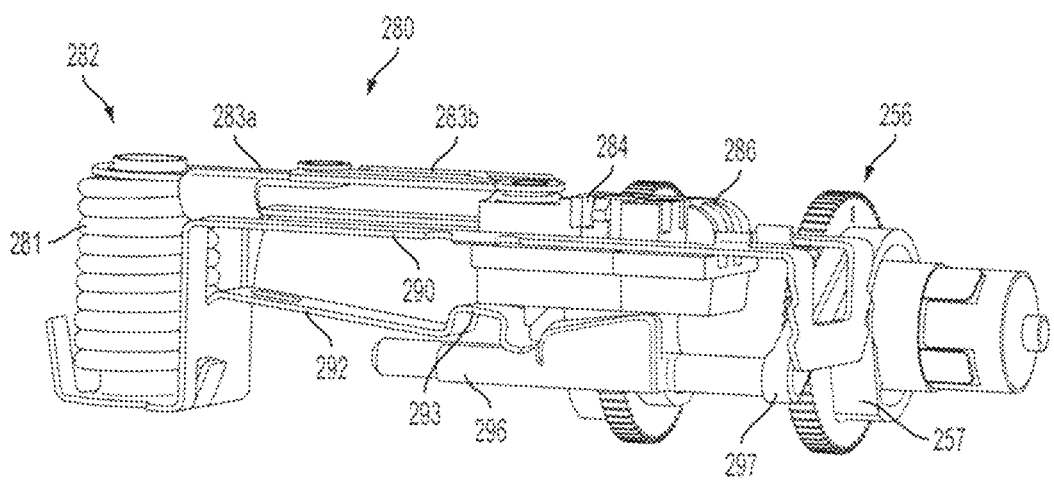
FIG. 8 is a side perspective view of the insertion mechanism shown in FIG. 7 in an intermediate position.

Another embodiment of an insertion mechanism 280 is shown in greater detail in FIGS. 7-10. The sliding members 284, 286 are slidably received in a frame 290 and moved by a spring-biased linkage mechanism 282 including torsion spring 281 and linkages 283a, 283b. In this embodiment, a cam finger 292 (e.g., extending from the frame 290) engages beneath one or both of the sliding members 284, 286 to lock the sliding members in the retracted or pre-deployment position (FIG. 7). In this pre-deployment position, the cam finger 292 is held against the sliding members 284, 286 by a release bar 296, which may be moved (rotated) to allow the cam finger 292 to move and release the sliding members 284, 286 (FIG. 8). The cam finger 292 may be biased in a downward direction and/or the second sliding member 286 may include a cam surface 287 to help facilitate movement along the cam finger 292 over locking mechanism 293 upon actuation.

The release bar 296 includes a lever 297 for pivoting the release bar 296 between an engaged position against the cam finger 292 (FIG. 7) and a disengaged position releasing the cam finger 292 (FIG. 8). The release bar 296 may be biased toward the disengaged position and held against the cam finger 292 in the engaged position until the lever 297 is released allowing the release bar 296 to move to the disengaged position. In the illustrated embodiment, the lever 297 engages a rotating surface 257 of a drive wheel 256 of the fluid drive mechanism 150 such that the lever 297 is held in the engaged position for part of the rotation and is released at a certain point during the rotation (e.g., when a flat portion of the rotating surface 257 allows the lever 297 to move).

Figure 9:
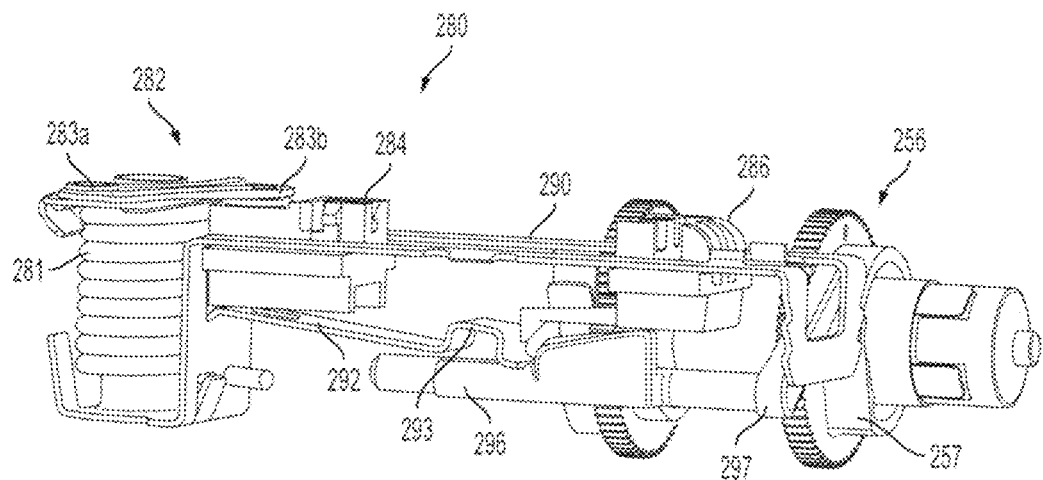
FIG. 9 is a side perspective view of the insertion mechanism shown in FIG. 7 in a post-deployment position.
Figure 10:
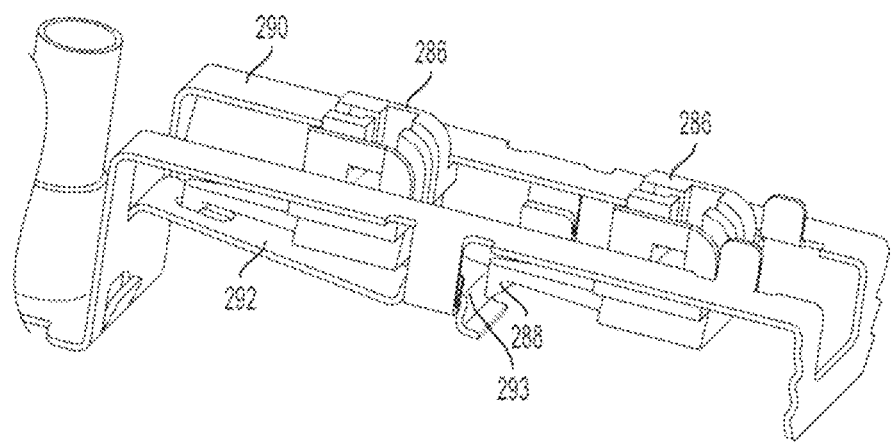
FIG. 10 is a top perspective view of the second sliding member of the insertion mechanism shown in FIG. 7 locked in the pre-deployment and post-deployment positions.

As shown in FIGS. 9 and 10, the cam finger 292 may also be used to lock the second sliding member 286 in the insertion position. A locking portion 288 of the second sliding member 286 engages a locking portion 293 of the cam finger 292 when the linkage mechanism 282 is fully extended in the intermediate position and prevents the second sliding member 286 from retracting such that the cannula remains inserted. As discussed above, the second sliding member 286 may also be locked by one or more latches (not shown) extending from a top of the frame 290.

Referring to FIGS. 11-16, one embodiment of the fluid drive mechanism 150 uses a clutch mechanism 160 to facilitate filling of the reservoir 130 and engagement of the fluid drive mechanism 150 for driving fluid out of the reservoir 130. The fluid drive mechanism 150 includes a first threaded member in the form of an elongated shaft such as a threaded drive rod or leadscrew 152, with external threads extending from a plunger 136 received in the reservoir 130 and sealed with an o-ring 137 against the inside surface of the reservoir 130. The leadscrew 152 and plunger 136 may be an inseparable, insert-molded assembly. A second threaded member in the form of an elongated shaft such as a tube nut 154 with internal threads threadably engages the leadscrew 152 and may be driven by a drive wheel 156 via a clutch mechanism 160.

When the reservoir 130 is empty (FIGS. 11 and 12), the plunger 136 is positioned at one end of the reservoir 130 such that the plunger 136 is extended and the clutch mechanism 160 is disengaged. In certain embodiments, the reservoir 130 may be filled with fluid by opening an inlet port to the reservoir 130 and pumping in the fluid under sufficient hydraulic pressure to retract the plunger 136 within the reservoir 130. Thereafter, the inlet port may be closed. When the reservoir 130 is filled and the plunger 136 moves to the opposite (retracted) end of the reservoir 130 (FIG. 13), the clutch mechanism 160 remains disengaged to allow the tube nut 154 to pass into an elongated cylindrical bore (along the drive axis) of a hub of the drive wheel 156. The clutch mechanism 160 may then be engaged (FIGS. 14-16) such that rotation of the drive wheel 156 causes the clutch mechanism 160 to rotate the tube nut 154, which causes the leadscrew 152 to advance the plunger into the reservoir 130 to deliver the fluid from the reservoir 130. In alternative embodiments, the reservoir 130 may be filled when the plunger 136 is already retracted.

Figure 11:
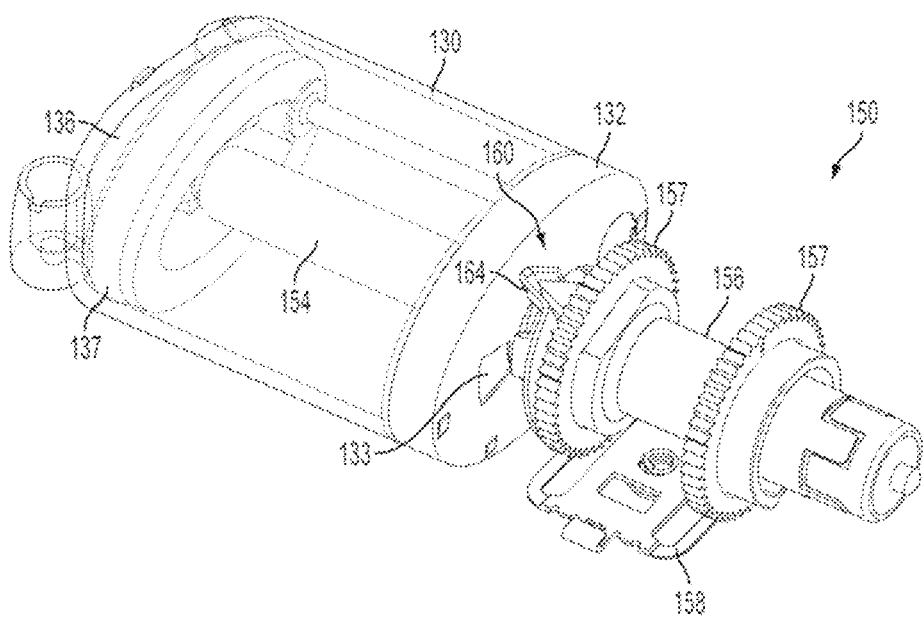
FIG. 11 is a top perspective view of a fluid driving mechanism of the fluid delivery device shown in FIG. 1 with a clutch mechanism in a disengaged position prior to filling.
Figure 12:
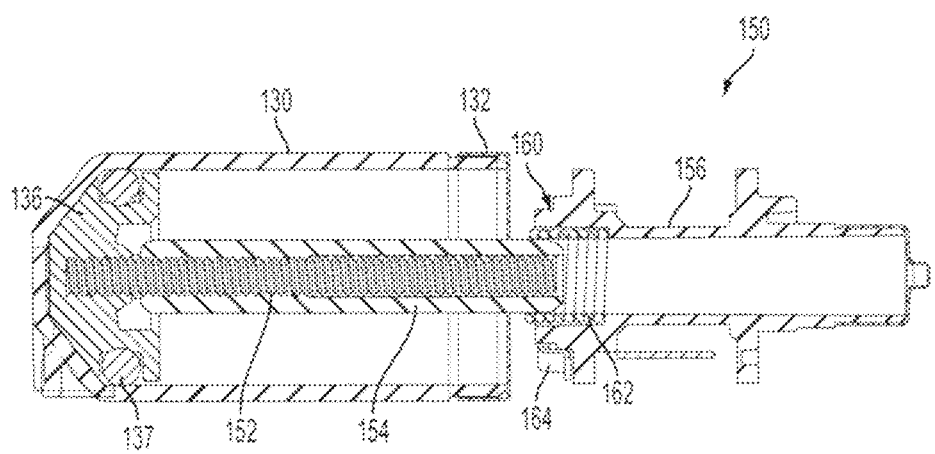
FIG. 12 is a side cross-sectional view of the fluid driving mechanism shown in FIG. 11.
Figure 13:
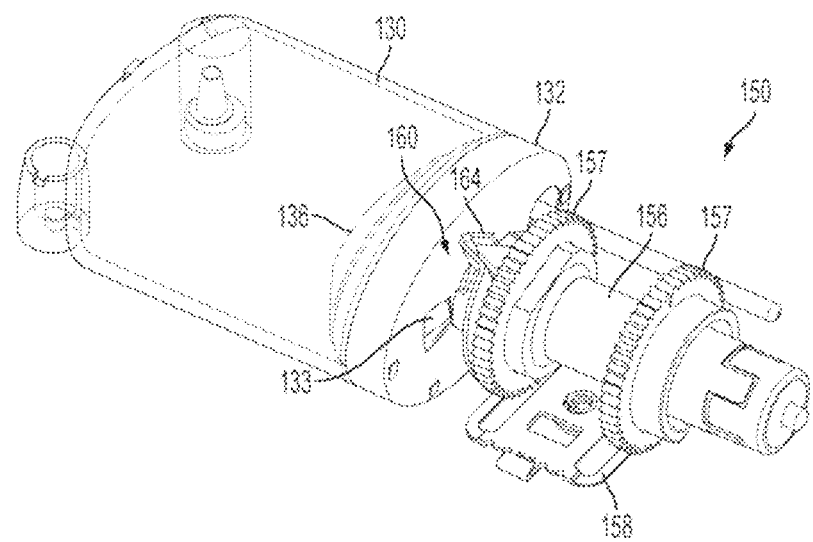
FIG. 13 is a top perspective view of the fluid driving mechanism shown in FIG. 11 with the clutch mechanism in a disengaged position after filling.
Figure 14:
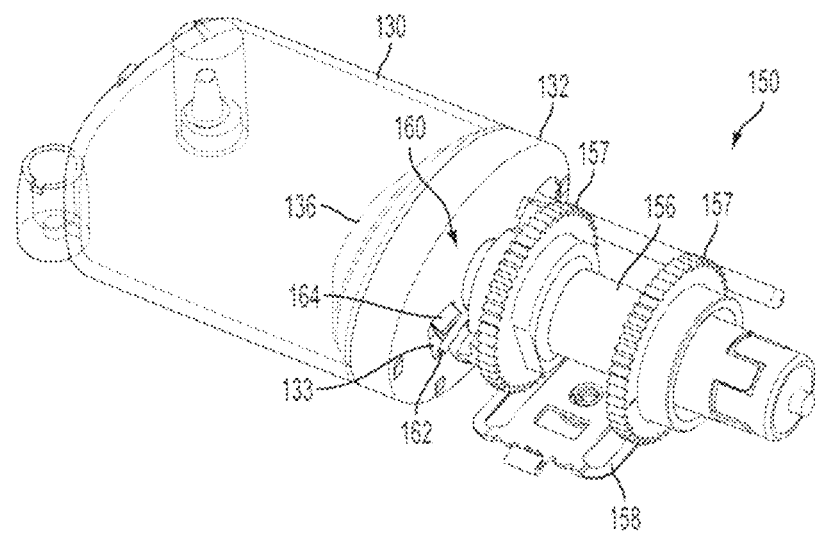
FIG. 14 is a top perspective view of the fluid driving mechanism shown in FIG. 11 with the clutch mechanism being released to the engaged position.
Figure 15:
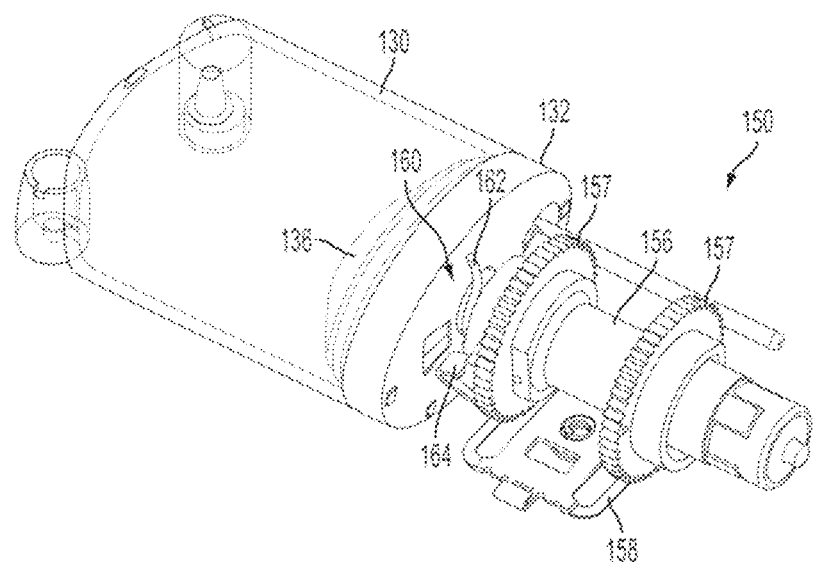
FIGS. 15 and 16 are top perspective views of the fluid driving mechanism shown in FIG. 11 with the clutch mechanism in the engaged position.
Figure 16:
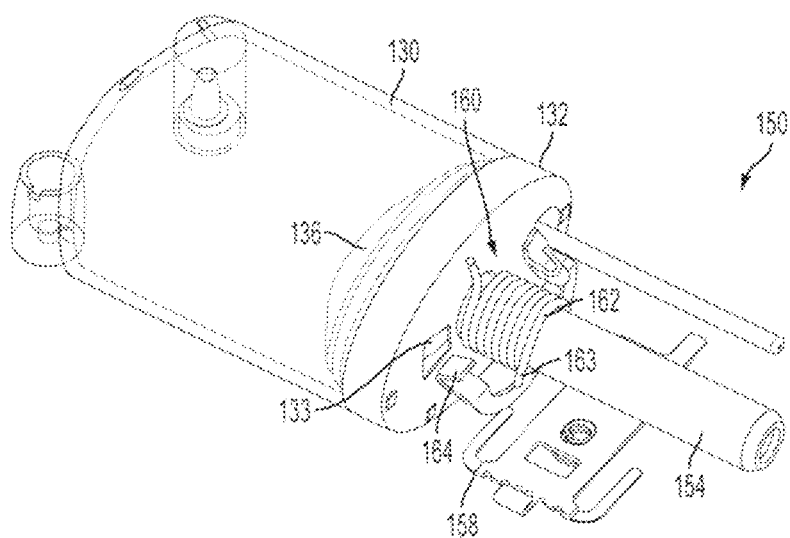
Figure 17:
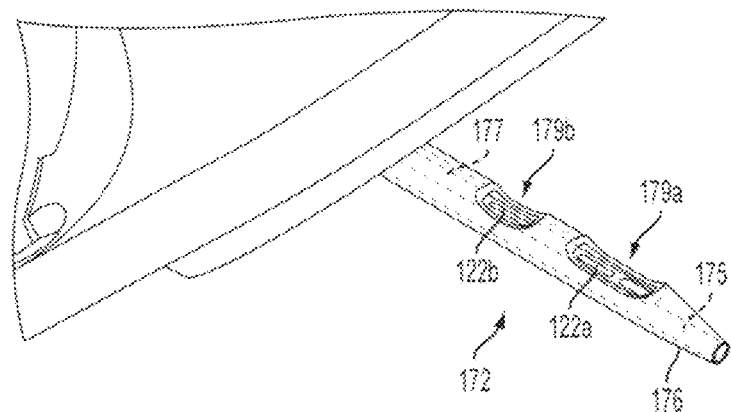
FIGS. 17-23 are views of a bi-lumen cannula used in the fluid delivery device shown in FIGS. 1-6 to insert a monitor test strip transcutaneously.
Figure 18:
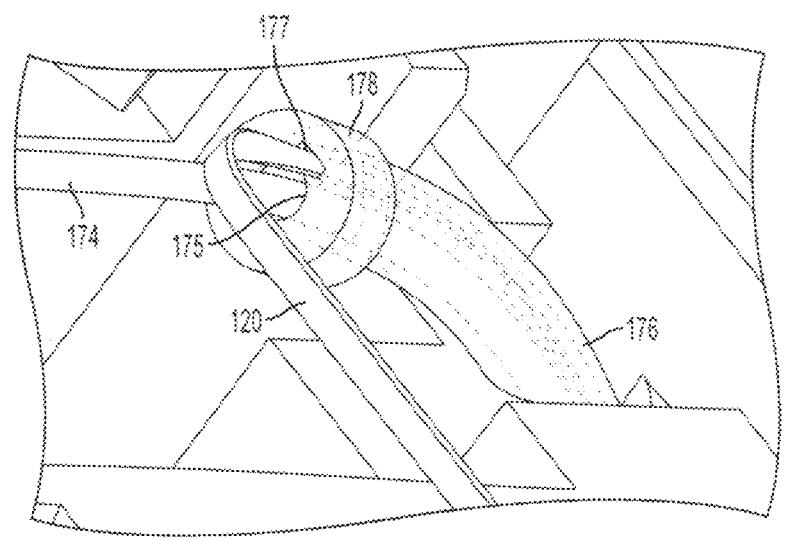
Figure 19:
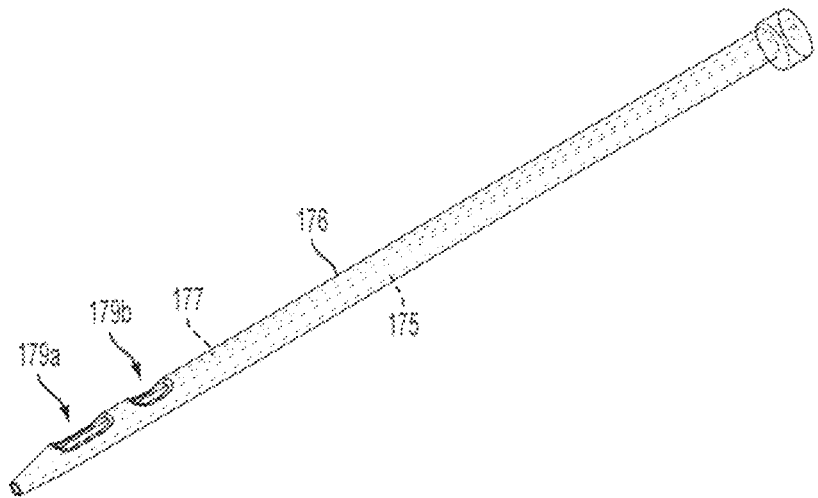
Figure 20:
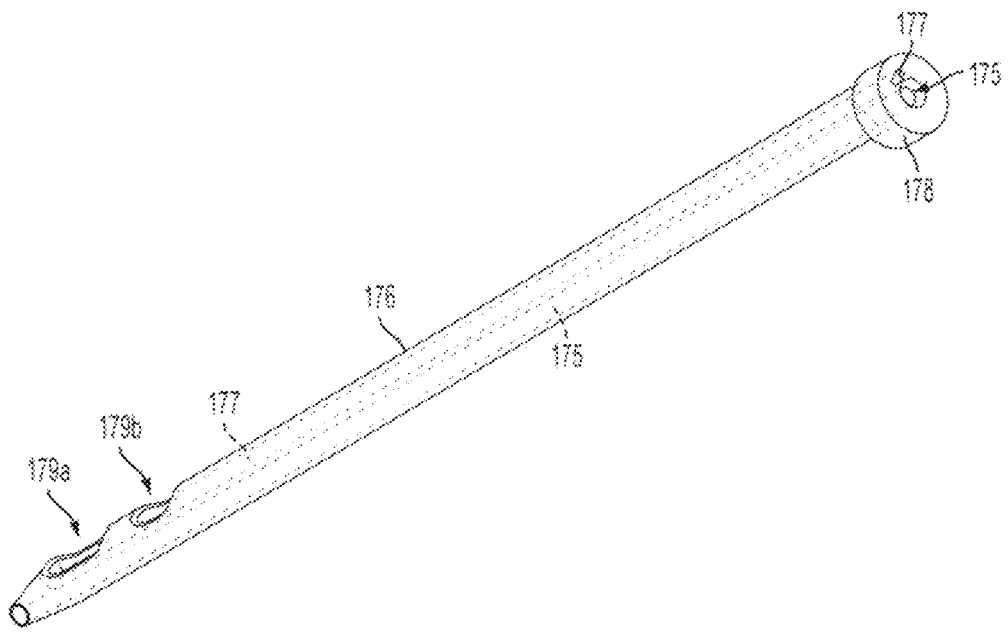
Figure 21:
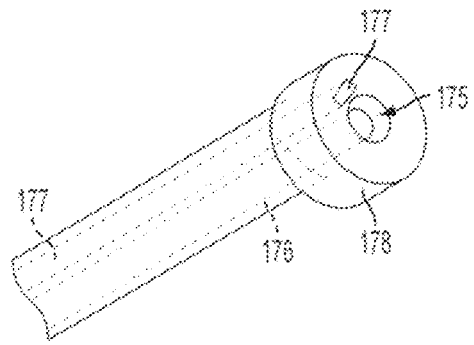
Figure 22:
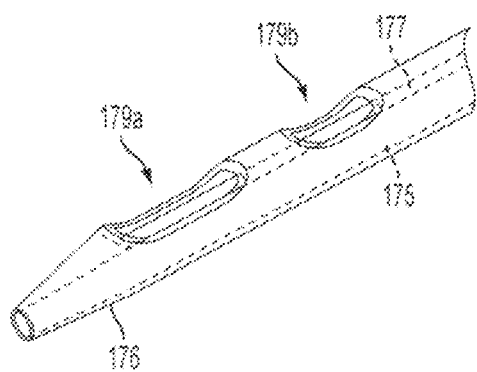
Figure 23:
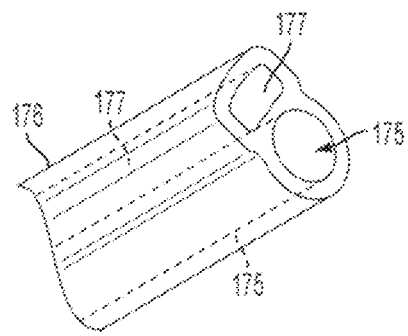
Figure 24:
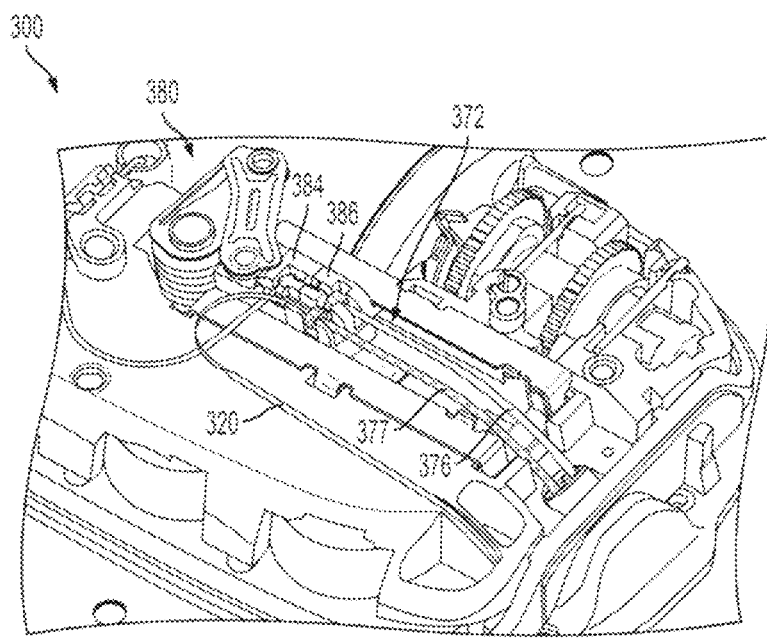
FIGS. 24-29 are views of another embodiment of a fluid delivery device including a cannula with a D-shaped lumen for inserting a monitor test strip transcutaneously.
Figure 25:
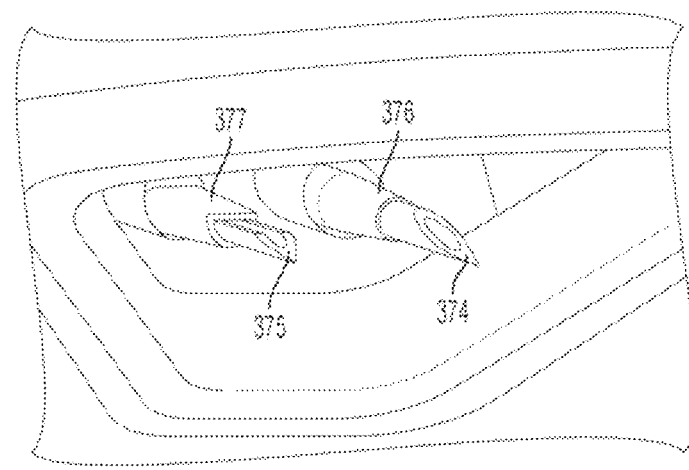
Figure 26:
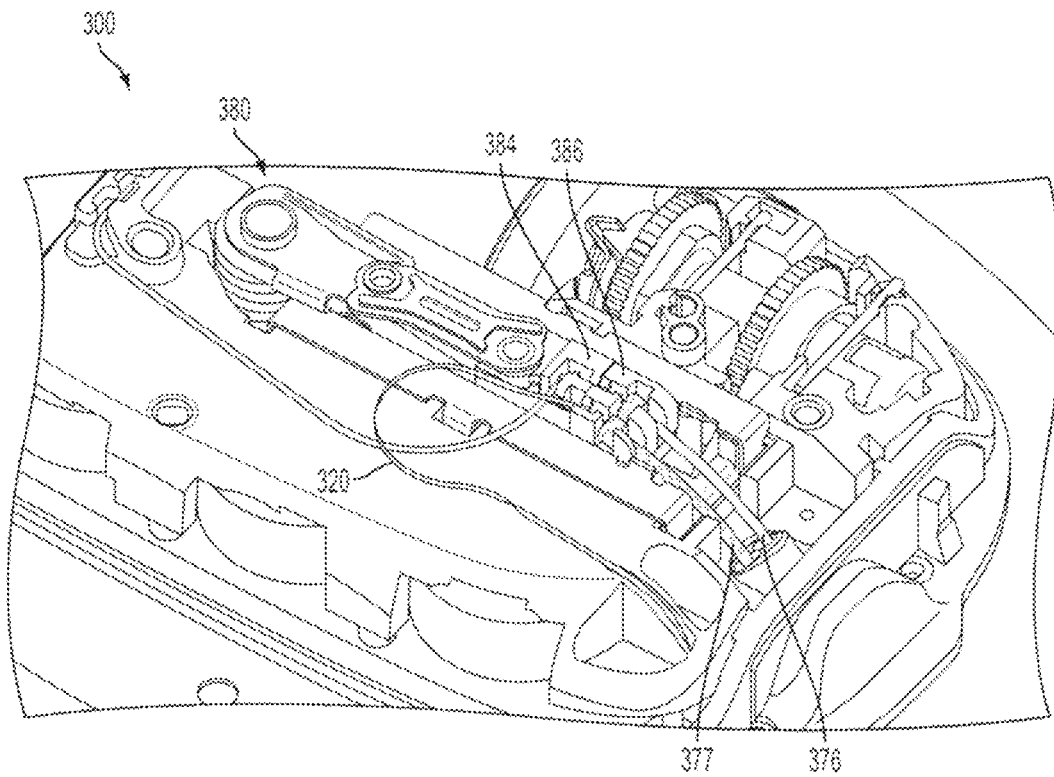
Figure 27:
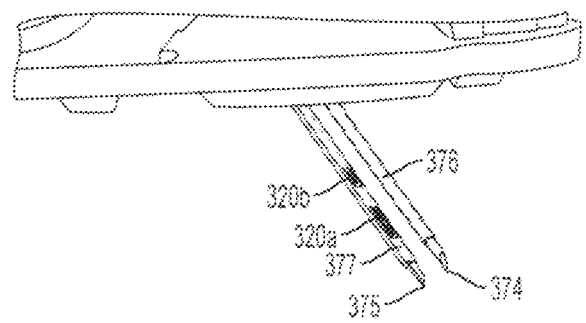
Figure 28:
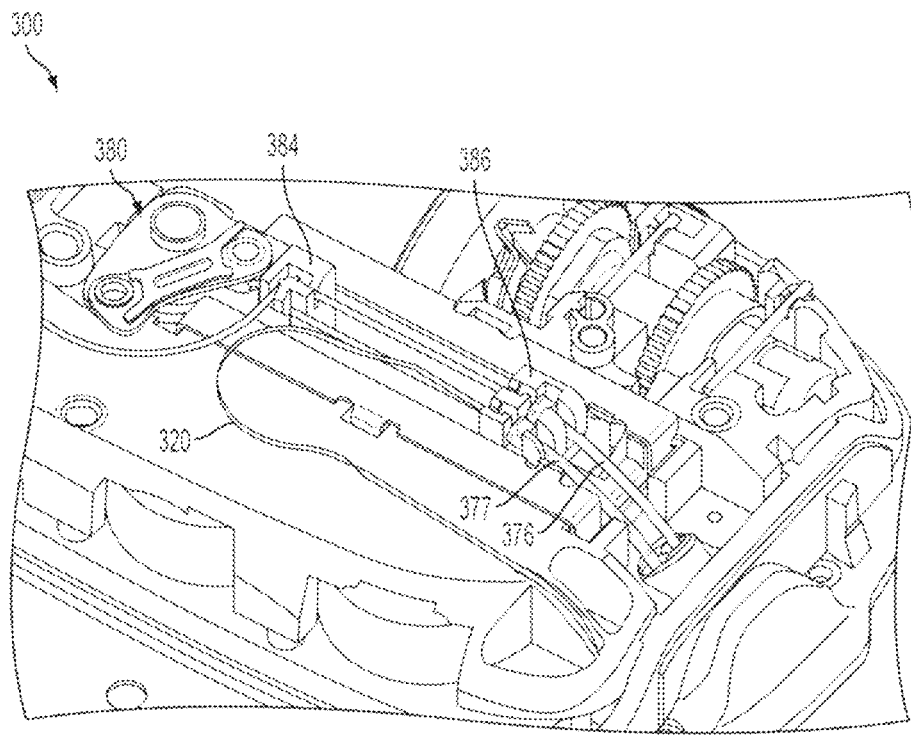
Figure 29:
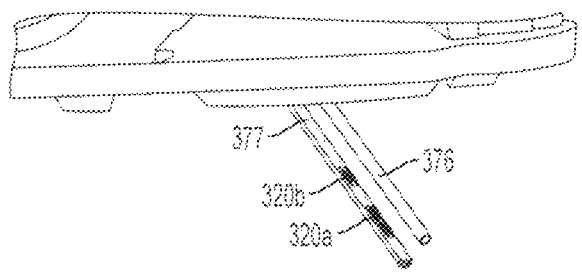
Figure 30:
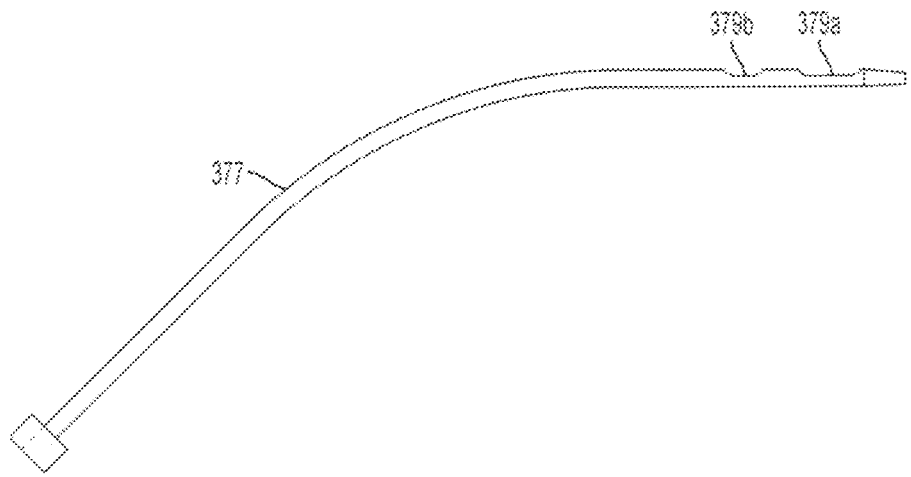
FIGS. 30-32 are views of the D-lumen cannula used in the fluid delivery device of FIGS. 24-29.
Figure 31:
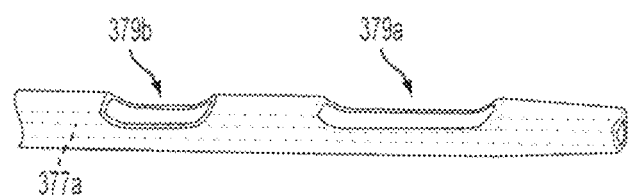
Figure 32:
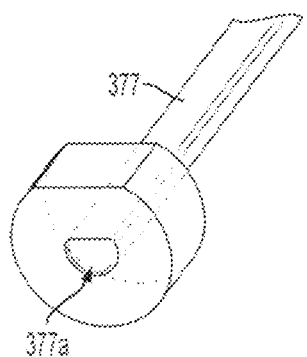
Figure 33:
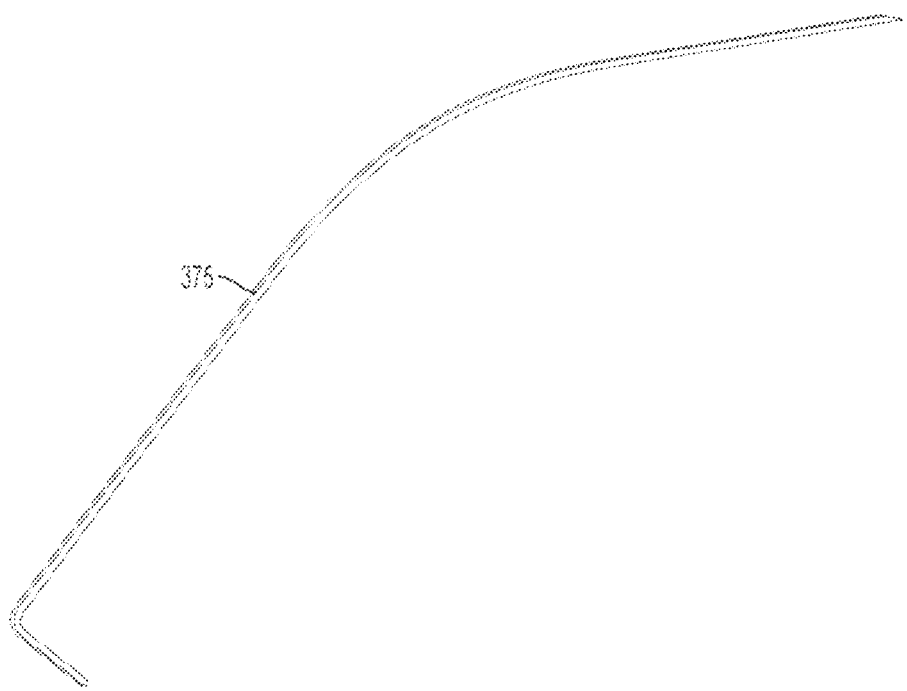
FIGS. 33 and 34 are views of a semi-circular trocar used with the D-lumen cannula in the fluid delivery device of FIGS. 18-23.
Figure 34:
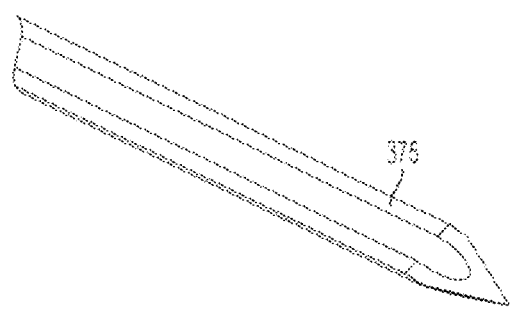
Figure 35:
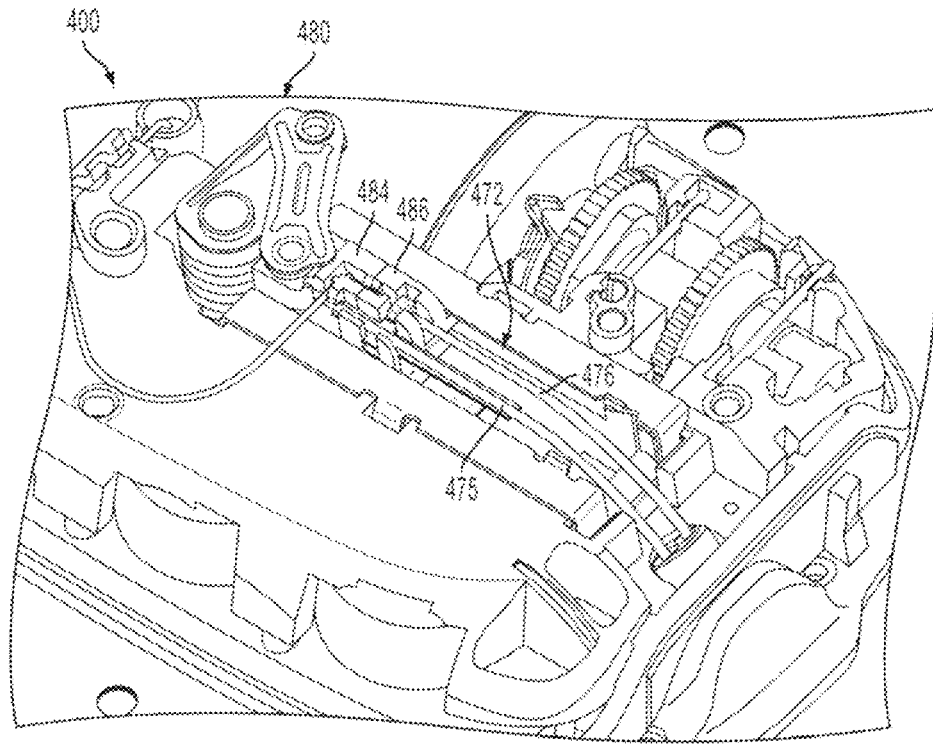
Figure 36:
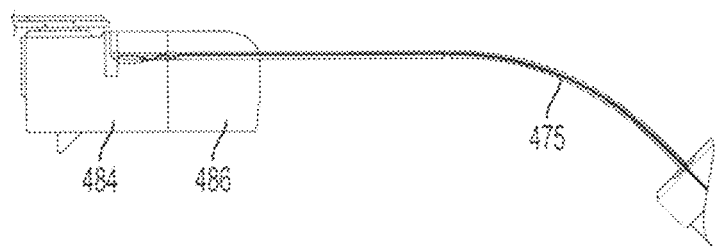
Figure 37:
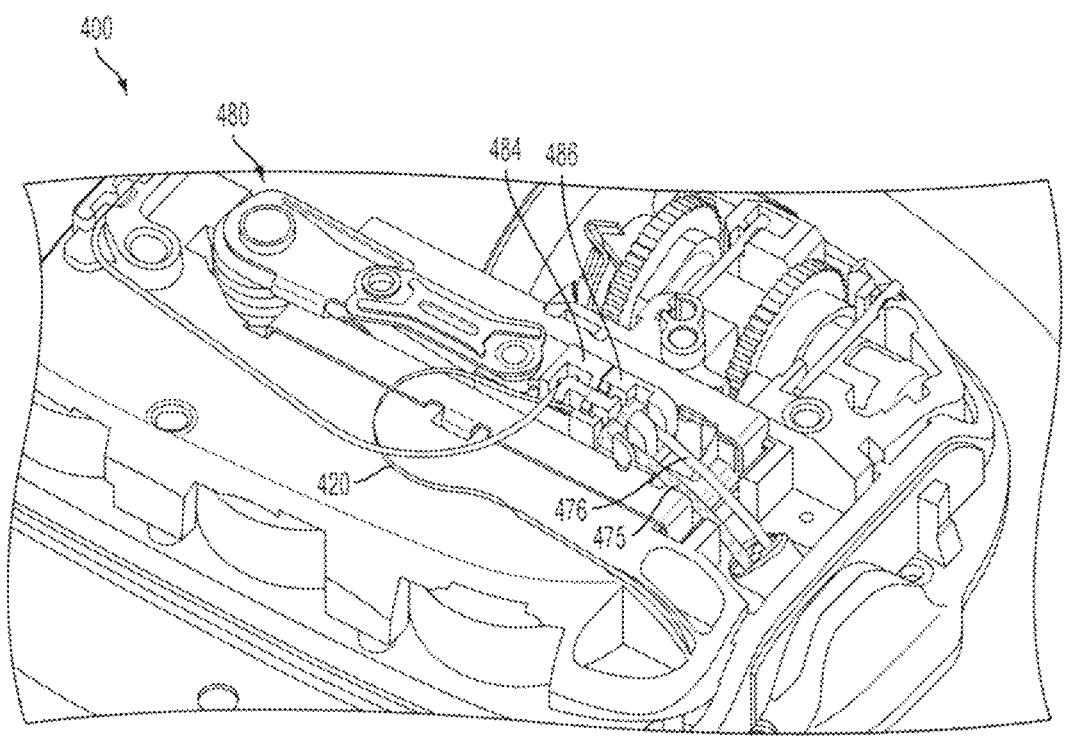
Figure 38:
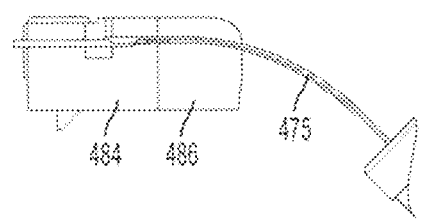

In the illustrated embodiment, the clutch mechanism 160 includes a clutch spring 162 (e.g., a helical torsion spring) located in a counterbore at one end of the drive wheel 156, adjacent the reservoir 130. The inside diameter of the clutch spring 162 is larger than the outside diameter of the tube nut 154 when the clutch spring 162 is loaded, thereby disengaging the clutch spring 162 from the tube nut 154 and allowing the tube nut 154 to pass through the center aperture of the spring 162 and into the elongated bore of the drive wheel 156. Alternatively, the inside diameter of the clutch spring 162 is smaller than the outside diameter of the tube nut 154 when the clutch spring 162 is unloaded, thereby engaging or gripping the tube nut 154 and allowing the drive wheel 156 to rotate the tube nut 154. In the illustrated embodiment, prior to filing the reservoir 130, the clutch spring 162 is held in the loaded, disengaged position by a spring latch 164 engaged with the drive wheel 156 (FIGS. 11-13). After the reservoir 130 has been filled, the clutch spring 162 may thus be engaged by rotating the drive wheel 156 until the spring latch 164 releases the clutch spring 162 (FIG. 14) allowing the clutch spring 162 to unload and grip the tube nut 154 (FIGS. 15 and 16), at which time fluid may be dispensed from the reservoir 130 with continued rotation of the drive wheel 156.

As shown, the spring latch 164 may be biased by the clutch spring 162 such that as the drive wheel 156 rotates the spring latch 164 moves rotationally against a surface of a reservoir cap 132 until clutch spring 162 deflects the spring latch 164 into a window 133 in the reservoir cap 132. When the spring latch 164 moves into the window 133, the end of the clutch spring 162 held by the spring latch 164 is released, thus engaging the clutch mechanism 160. When the clutch spring 162 is engaged, the drive wheel 156 contacts an end 163 of the clutch spring 162 to create a thrust on the clutch spring 162 that causes the clutch spring 162 to rotate the tube nut 154. The fluid drive mechanism 150 may also use other clutch mechanisms capable of allowing the tube nut 154 or other type of nut or threaded member to pass through the clutch mechanism and then being activated to engage the nut or threaded member.

In the illustrated embodiment, the drive wheel 156 includes ratchets 157 that are engaged by an actuator 158 to incrementally drive the wheel 156 and advance the plunger 136 into the reservoir 130. Examples of this actuation mechanism are described in greater detail in U.S. Patent Application Publication No. 2005/0238507, which is fully incorporated herein by reference.

By using a clutch mechanism, the engagement between the leadscrew and the nut occurs at assembly, and thus no rotation is needed for the nut to engage the leadscrew by operation of the device. This reduces the number of fluid path prime pulses to prime the pump and assures a full and proper priming of the fluid path before placement on the body. The clutch mechanism also enables the changing of thread pitch for other drug applications without a need to redesign the tilt nut used in fluid driving mechanisms in other existing pumps. The components of the clutch mechanism are also more easily inspected than the tilt nut assembly.

According to one embodiment, as shown in FIGS. 17-23, the cannula 176 providing the transcutaneous access for delivery the fluid may also be used to introduce the monitor test strip 120. In this embodiment, the cannula 176 includes a first lumen 175 for receiving the needle/trocar 174 and a second lumen 177 for receiving the test strip 120. As shown, the first lumen 175 has a circular (cylindrical) profile and the second lumen 177 has a rectangular profile. The cannula 176 may also include one or more windows 179a, 179b providing access to one or more sensors 122a, 122b on the test strip 120. As shown, the plurality of windows 179a, 179b of the cannula 176 may be arranged on a same side of the sidewall of cannula 176, with the first window 179a arranged at a distance from the distal end tip of the cannula 176 which is less than the distance of the second window 179b from the distal end tip of the cannula 176.

To insert the test strip 120 into second lumen 177, the test strip 120 passes into second lumen 177 at the head 178 of the cannula 176 and extends to the window(s) 179a, 179b. Thus, at least one window 179a, 179b exposes a sensor 122a, 122b of the monitoring test strip 120. In the example embodiment, two windows 179a, 179b are provided with the window 179a closest to the tip of the cannula 176 providing access to the main sensor area and the window 179b farthest from the tip providing a reference. Although a specific shape and configuration of a bi-lumen cannula is shown, other configurations of a cannula with first and second lumens may also be used to both deliver a therapeutic fluid and introduce a test strip subcutaneously.

According to another embodiment, as shown in FIGS. 24-34, a fluid delivery device 300 may include a transcutaneous access tool 372 with a first cannula 376 for delivering fluid and a second cannula 377 for introducing a test strip 320. The first cannula 376 receives a first needle/trocar 374 (shown as a circular needle) to facilitate insertion of the first cannula 376 and the second cannula 377 receives a second needle/trocar 375 (shown as a semi-circular trocar) to facilitate insertion of the second cannula 377. The fluid deliver device 300 includes an insertion mechanism 380, similar to the first described embodiment above, but with sliding members 384, 386 coupled to both the needle 374 and the trocar 375 and both cannulas 376, 377. The insertion mechanism 380 inserts the second cannula 377 and the trocar 375 and then retracts the trocar 375 in the same manner as described above. The test strip 320 remains inserted after the trocar 375 is retracted. Thus, both the first needle/trocar 374 and the second needle/trocar 375 may be introduced into the patient simultaneously, particularly to reduce the pain of sequential insertions.

Similar to the above described embodiment, first cannula 376 includes a circular (cylindrical) lumen 376a. As shown in greater detail in FIGS. 30-32, the second cannula 377 includes a semi-circular (D-shaped) lumen 377a to allow the monitor strip to sit relatively flat within the cannula 377. The second cannula 377 also includes one or more windows 379a, 379b providing access to one or more sensors 320a, 320b on the test strip 320 (see FIGS. 27 and 29). As shown, similar to the prior embodiment, the plurality of windows 379a, 379b, of the cannula 377 may be arranged on a same side of the sidewall of the cannula 377, with the first window 379a arranged at a distance from the distal end tip of the cannula 377 which is less than the distance of the second window 379b from the distal end tip of the cannula 377. Thus, at least one window 379a, 379b exposes a sensor 320a, 320b of the monitoring test strip 320. In the example embodiment, two windows 379a, 379b are provided with the window 379a closest to the tip of the cannula 377 providing access to the main sensor area and the window 379b farthest from the tip providing a reference. As shown in greater detail in FIGS. 33 and 34, the trocar 375 has a shape corresponding to the D-shaped lumen 377a to allow the trocar 375 to be retracted leaving the test strip 320 inserted (see FIG. 29). As shown, the trocar includes a planar side surface 373 which corresponds to a planar test strip 320 such that, when assembled, the planar test strip 320 may be located adjacent the planar side surface 373 of the trocar 375 in the second cannula 377.

According to another embodiment, as shown in FIGS. 35-43, a fluid delivery device 400 may include a transcutaneous access tool 472 with a cannula 476 for delivering fluid and a needle or trocar 475 (shown as a semi-circular trocar) for introducing a test strip 420. The cannula 476 receives a needle/trocar 474 (shown as circular needle) to facilitate insertion of the cannula 476 and the trocar 475 is inserted with the test strip 420. The fluid deliver device 400 includes an insertion mechanism 480, similar to the first described embodiment above, but with sliding members 484, 486 coupled to both the needle 474 and the trocar 475. The insertion mechanism 480 inserts the trocar 475 (FIGS. 37 and 38) and then retracts the trocar 475 (FIGS. 39 and 40) in the same manner as the needle/trocar described above. The test strip 420 remains inserted after the trocar 475 is retracted (FIG. 41). In contrast to the prior embodiment, the needle/trocar 475 introduces the monitoring test strip 420 subcutaneously solely (i.e. without the monitoring test strip 420 being introduced with a cannula).

Figure 42:
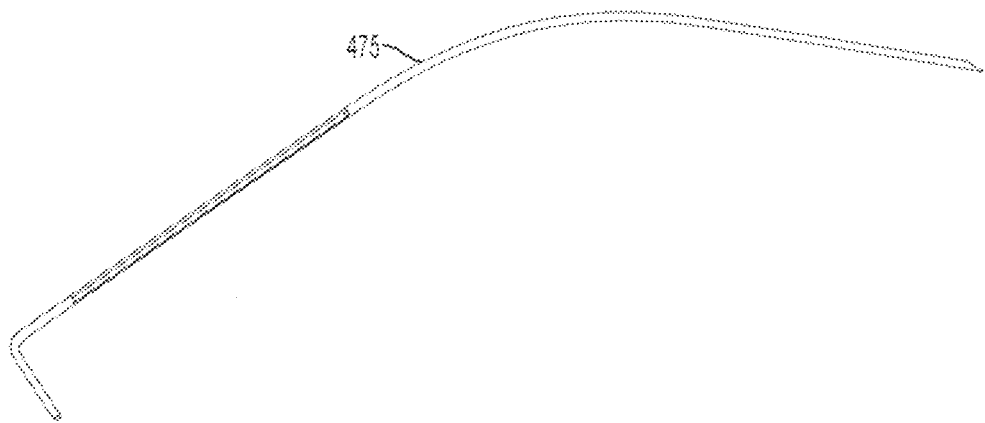
FIG. 42 is a side view of the oval trocar for use in the fluid delivery device shown in FIGS. 35-41.
Figure 43:
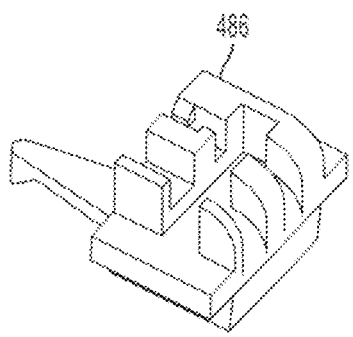
FIG. 43 is a top perspective view of a second sliding member for use in the fluid delivery device shown in FIGS. 35-41.

The trocar 475 is shown in greater detail in FIG. 42. The second sliding member 486 is shown in greater detail in FIG. 43. In this embodiment, the second sliding member 486 is designed to capture the cannula 476 and to receive and allow the trocar 475 to pass through.

Accordingly, various embodiments of the fluid delivery device may use the transcutaneous access tool both to deliver fluid and to introduce a test strip subcutaneously to provide integrated monitoring.

In certain embodiments, an operational sequence of fluid delivery device 100 (or 300 or 400) of the present disclosure may be automatically triggered or otherwise initiated based upon a filling of the fluid reservoir 130 with a fluid to a predetermined fill level. For example, the fluid reservoir 130 may include a fluid fill sensor which provides feedback of the fluid fill level, which may be an input to a computer instruction program stored in non-transitory memory and run by a computer processor stored and located with the circuit board 101 of the fluid delivery device 100.

Prior to the fluid reservoir 130 being filled with fluid, the fluid delivery device 100, and more particularly the computer processor, may be in a stand-by (e.g. sleep) mode. Once the computer processor detects an input signal from the fluid fill sensor that the fluid in the fluid reservoir 130 has reached the predetermined fill level, the computer processor may execute a computer program which includes instructions to automatically operate the transcutaneous access tool insertion mechanism 180 within a transcutaneous access tool introduction time period, which may also be understood as a predetermined deployment time period, i.e. the time period between the filling of the fluid reservoir 130 and the insertion of the needle/trocar 174 and cannula 176 through the skin of a patient.

For example, a clinician may fill the fluid reservoir 130 with a therapeutic fluid at a clinic, which results in the fluid fill sensor sending an input signal which is detected by the computer processor as to the filled status of the fluid reservoir 130. Upon receiving the input signal from the fluid fill sensor, the operational computer program for the fluid delivery device 100 being run by the computer processor may instruct the fluid delivery device 100 to operate the transcutaneous access tool insertion mechanism 180 within the transcutaneous access tool introduction time period. During the transcutaneous access tool introduction time period, the clinician may properly position and locate the fluid delivery device 100 on the patient. The transcutaneous access tool introduction time period should be long enough to properly install the fluid delivery device 100 on the patient, but not so long that the clinician and patient have to wait a substantial time for the transcutaneous access tool insertion mechanism 180 to operate.

In certain embodiments, the transcutaneous access tool introduction time period may be greater than or equal to 30 seconds, and less than or equal to 15 minutes. More particularly, the transcutaneous access tool introduction time period may be greater than or equal to 1 minute, and less than or equal to 10 minutes. Even more particularly, the transcutaneous access tool introduction time period may be greater than or equal to 2 minutes, and less than or equal to 5 minutes.

It may also be desirable to delay the onset of infusion for an infusion delay time period after insertion of the needle/trocar 174 and cannula 176 through the skin of a patient. For example, it may be desirable to delay infusion of the fluid from fluid reservoir 130 if such may adversely react with, or be rendered less effective by, a first composition already in the patient, such as another therapeutic composition, which may also be a therapeutic fluid.

In such instance, it may be desirable to automatically delay infusion of the fluid from fluid reservoir 130 until the first therapeutic composition in the patient decreases to levels of less than 20% (and more particularly less than 10%, and even more particularly less than 5%) of a concentration level in the patient as compared to the concentration level when the first therapeutic composition is introduced to the patient.

Given that it may not be possible to accurately predict the rate of decrease in concentration of a therapeutic composition in the patient, it may be desirable to delay infusion of the fluid from fluid reservoir 130 for a predetermined infusion delay time period.

For example, the infusion delay time period between the insertion of the needle/trocar 174 and cannula 176 through the skin of a patient and the infusion of the fluid from the fluid reservoir may be at least 1 hour. In other embodiments, the infusion delay time period may be at least 2 hours, at least 4 hours, at least 8 hours, at least 12 hours, at least 16 hours, at least 20 hours, at least 24 hours, at least 28 hours, at least 32 hours, at least 36 hours, at least 40 hours, at least 44 hours, at least 48 hours, at least 52 hours, at least 56 hours, at least 60 hours, at least 64 hours, at least 68 hours or at least 72 hours.

While the principles of the invention have been described herein, it is to be understood by those skilled in the art that this description is made only by way of example and not as a limitation as to the scope of the invention. Other embodiments are contemplated within the scope of the present invention in addition to the exemplary embodiments shown and described herein. Modifications and substitutions by one of ordinary skill in the art are considered to be within the scope of the present invention, which is not to be limited except by the following claims.

What is claimed is:

1. A medical device, comprising:
   an infusion device comprising a fluid reservoir and a transcutaneous access tool fluidly coupled to the fluid reservoir, the transcutaneous access tool configured to deliver a therapeutic fluid subcutaneously to a patient,
   wherein the infusion device operates in a stand-by mode prior to the therapeutic fluid being introduced into the fluid reservoir and in the stand-by mode during filling of the fluid reservoir to a predetermined fill level with the therapeutic fluid,
   wherein the infusion device is operable to generate a signal indicative that the fluid reservoir has been filled, and upon generating the signal indicative that the fluid reservoir has been filled, the infusion device uses the signal to cause infusion of the therapeutic fluid from the fluid reservoir after a predetermined infusion delay time period.

2. The medical device of claim 1, wherein the infusion device comprises non-transitory memory including stored instructions that, when executed by at least one processor, cause the infusion device to infuse the therapeutic fluid from the fluid reservoir after the predetermined infusion delay time period.

3. The medical device of claim 2, wherein the infusion device comprises at least one sensor, wherein the at least one sensor operates by sending an input signal to the at least one processor in response to the occurrence of the fluid reservoir being filled.

4. The medical device of claim 3, wherein the at least one processor operates by detecting the input signal from the at least one sensor and, upon detecting the input signal from the at least one sensor, the at least one processor operates to execute the stored instructions that cause the infusion device to infuse the therapeutic fluid from the fluid reservoir after the predetermined infusion delay time period.

5. The medical device of claim 1, wherein the predetermined infusion delay time period is greater than or equal to 60 minutes.

6. The medical device of claim 1, wherein the predetermined infusion delay time period is greater than or equal to 2 hours.

7. The medical device of claim 1, wherein the predetermined infusion delay time period is at least 8 hours.

8. The medical device of claim 1, wherein the predetermined infusion delay time period is at least 24 hours.

9. The medical device of claim 1, wherein the fluid reservoir comprises:
   a fluid fill sensor operable to provide feedback of the fluid fill level.

10. The medical device of claim 9, wherein the insertion mechanism is configured to insert the needle/trocar with an increasing insertion force as the needle/trocar moves in an insertion direction.

11. The medical device of claim 9, wherein the insertion mechanism comprises:
    a spring-biased linkage mechanism operable to move a first sliding member in both an insertion direction and a retraction direction.

12. The medical device of claim 1, wherein the transcutaneous access tool comprises:
    an insertion mechanism; and
    a needle/trocar, wherein the insertion mechanism is configured to insert and retract the needle/trocar in a single uninterrupted motion.

13. The medical device of claim 1, wherein the transcutaneous access tool comprises:
    an insertion mechanism including a spring-biased linkage mechanism, a first sliding member and a second sliding member.

14. The medical device of claim 13, wherein the first sliding member and the second sliding member are coupled to a needle/trocar and cannula.

15. The medical device of claim 1, wherein the transcutaneous access tool comprises:
    an insertion mechanism including a helical torsion spring, a first linkage and a second linkage, wherein the first linkage and the second linkage are coupled between the helical torsion spring and a first sliding member.

16. The medical device of claim 15, wherein the helical torsion spring is operable to provide a continuous uninterrupted rotation of the first linkage to enable the insertion and retraction of the needle/trocar in a single, uninterrupted motion.

17. A medical device, comprising:
    an infusion device comprising a fluid reservoir and a transcutaneous access tool fluidly coupled to the fluid reservoir, the transcutaneous access tool configured to deliver a therapeutic fluid subcutaneously to a patient, wherein:
    the infusion device operates in a stand-by mode prior to the therapeutic fluid being introduced into the fluid reservoir and in the stand-by mode during filling of the fluid reservoir to a predetermined fill level with the therapeutic fluid,
    the infusion device is operable to generate a signal indicative that the fluid reservoir has been filled, and upon generating the signal indicative that the fluid reservoir has been filled, the infusion device uses the signal to cause infusion of the therapeutic fluid from the fluid reservoir after a predetermined infusion delay time period, and
    the predetermined infusion delay time period is a time sufficient to allow a first therapeutic composition already in the patient to decrease from a first concentration level in the patient when the first therapeutic composition was introduced to the patient to a second concentration level in the patient.

18. The medical device of claim 17, wherein the second concentration level is less than 20% of the first concentration level.

19. The medical device of claim 17, wherein the second concentration level is less than 10% of the first concentration level.

20. The medical device of claim 17, wherein the second concentration level is less than 5% of the first concentration level.

\* \* \* \* \*